United States Patent
Dorn, II

(10) Patent No.: US 11,083,699 B2
(45) Date of Patent: *Aug. 10, 2021

(54) TRANS-4-HYDROXYCYCLOHEXYL PHENYL AMIDE MITOFUSIN ACTIVATORS AND METHODS OF USE THEREOF

(71) Applicant: MITOCHONDRIA EMOTION, INC., Hamilton, OH (US)

(72) Inventor: Gerald W. Dorn, II, Hamilton, OH (US)

(73) Assignee: Mitochondria Emotion, Inc., Hamilton, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/935,557

(22) Filed: Jul. 22, 2020

(65) Prior Publication Data

US 2020/0345668 A1 Nov. 5, 2020

Related U.S. Application Data

(63) Continuation-in-part of application No. PCT/US2020/014784, filed on Jan. 23, 2020.

(60) Provisional application No. 62/949,060, filed on Dec. 17, 2019, provisional application No. 62/797,513, filed on Jan. 28, 2019.

(51) Int. Cl.
  A61K 31/165 (2006.01)
  A61P 25/28 (2006.01)
  A61K 31/27 (2006.01)

(52) U.S. Cl.
  CPC ............ *A61K 31/165* (2013.01); *A61K 31/27* (2013.01); *A61P 25/28* (2018.01)

(58) Field of Classification Search
  None
  See application file for complete search history.

(56) References Cited

U.S. PATENT DOCUMENTS

| | | |
|---|---|---|
| 4,438,130 A | 3/1984 | Kaplan |
| 4,463,013 A | 7/1984 | Collins et al. |
| 4,466,977 A | 8/1984 | McMillan et al. |
| 4,588,591 A | 5/1986 | Kaplan et al. |
| 4,618,621 A | 10/1986 | Tang |
| 4,632,935 A | 12/1986 | Kaplan |
| 4,656,182 A | 4/1987 | Horwell |
| 4,677,122 A | 6/1987 | Horwell |
| 4,737,493 A | 4/1988 | Horwell |
| 4,801,604 A | 1/1989 | Vonvoigtlander et al. |
| 4,855,316 A | 8/1989 | Horwell et al. |
| 5,051,428 A | 9/1991 | Horwell et al. |
| 5,063,242 A | 11/1991 | Horwell et al. |
| 5,366,987 A | 11/1994 | Lee et al. |
| 5,721,276 A | 2/1998 | Lesieur et al. |
| 6,127,159 A | 10/2000 | Fuller et al. |
| 6,284,507 B1 | 9/2001 | Fuller et al. |
| 6,953,680 B2 | 10/2005 | Fuller et al. |
| 7,662,910 B2 | 2/2010 | Hammock et al. |
| 7,727,717 B2 | 6/2010 | Vance et al. |
| 7,989,500 B2 | 8/2011 | Bhat et al. |
| 8,206,922 B2 | 6/2012 | Vance et al. |
| 8,226,928 B1 | 7/2012 | Sung et al. |
| 8,354,094 B1 | 1/2013 | Sung et al. |
| 8,361,439 B1 | 1/2013 | Sung et al. |
| 8,466,140 B2 | 6/2013 | Altieri et al. |
| 8,574,544 B1 | 11/2013 | Sung et al. |
| 8,604,244 B2 | 12/2013 | Bhat et al. |
| 8,791,069 B1 | 7/2014 | Sung et al. |
| 8,975,020 B2 | 3/2015 | Vance et al. |
| 9,238,625 B2 | 1/2016 | Bhat et al. |
| 9,296,681 B2 | 3/2016 | Bhat et al. |
| 9,388,156 B2 | 7/2016 | Blaauw et al. |
| 9,603,890 B2 | 3/2017 | Mann |
| 9,708,411 B2 | 7/2017 | Shi |
| 9,987,294 B2 | 6/2018 | Altieri et al. |
| 10,059,748 B2 | 8/2018 | Dunia et al. |
| 10,113,163 B2 | 10/2018 | Liu et al. |
| 10,119,142 B2 | 11/2018 | Choi et al. |

(Continued)

FOREIGN PATENT DOCUMENTS

| | | |
|---|---|---|
| WO | 2009114700 A1 | 9/2009 |
| WO | 2016054083 A1 | 4/2016 |

(Continued)

OTHER PUBLICATIONS

Chandhok et al., "Structure, function, and regulation of mitofusin-2 in health and disease", Biological Reviews, 2018 (published online Oct. 25, 2017), pp. 933-949.*
Schafer et al., "Failure is an option: learning from unsuccessful proof-of-concept trials", Drug Discovery Today, 2008, vol. 13 (21/22 ), pp. 913-916.*
Horig et al., "From bench to clinic and back: Perspective on the 1st IQPC Translational Research conference", Journal of Translational Medicine, 2004, vol. 2(44), 8 pages.*
J. G. Cannon, Burger's Medicinal Chemistry and Drug Discovery, Fifth Edition, vol. I: Principles and Practice, Wiley-Interscience 1995, Chapter Nineteen, pp. 783-802.*
Pubchem 249951 deposited Mar. 26, 2005 (Mar. 26, 2005) p. 1-9.
Huang et al. 'A Quantitative Assay for Mitochondrial Fusion Using Renilla Luciferase Complementation', Mitochondrion, 2010, vol. 10, pp. 559-566.

(Continued)

*Primary Examiner* — Savitha M Rao
*Assistant Examiner* — Gregg Polansky
(74) *Attorney, Agent, or Firm* — Vorys, Sater, Seymour and Pease LLP

(57) ABSTRACT

Compounds and compositions including stereoisomers of 6-phenylhexanamide derivative small molecule mitofusin activators are described. In particular, mitofusin activators comprising derivatives of (trans-4-hydroxycyclohexyl)-6-phenylhexanamide, which are useful for treating diseases or disorders associated with a mitochondria-associated disease, disorder, or condition such as diseases or disorders associated with mitofusin-1 (MFN1) and/or mitofusin-2 (MFN2), or mitochondrial dysfunction, are described. Methods of treatment and pharmaceutical formulations are also described.

18 Claims, 9 Drawing Sheets

(56) References Cited

U.S. PATENT DOCUMENTS

| | | | |
|---|---|---|---|
| 10,143,719 B2 | 12/2018 | Qi | |
| 10,245,297 B2 | 4/2019 | Mochly-Rosen et al. | |
| 10,301,356 B2 | 5/2019 | Hakansson | |
| 10,485,782 B2 | 11/2019 | Rinsch et al. | |
| 10,494,611 B2 | 12/2019 | Cho et al. | |
| 10,526,418 B2 | 1/2020 | Shi | |
| 10,578,610 B2 | 3/2020 | Mochly-Rosen et al. | |
| 10,617,664 B2 | 4/2020 | Pahan et al. | |
| 10,640,498 B2 | 5/2020 | Gibson et al. | |
| 10,709,724 B2 | 7/2020 | Alvarez et al. | |
| 10,723,737 B2 | 7/2020 | Hertz et al. | |
| 10,744,178 B2 | 8/2020 | Wilson | |
| 10,815,211 B2 | 10/2020 | Beyrath et al. | |
| 10,844,023 B2 | 11/2020 | Dorn et al. | |
| 2004/0152715 A1 | 8/2004 | Kawai et al. | |
| 2011/0256565 A1 | 10/2011 | Schon et al. | |
| 2011/0268722 A1 | 11/2011 | Siegelin et al. | |
| 2011/0275670 A1 | 11/2011 | Chapman et al. | |
| 2012/0164243 A1 | 6/2012 | Rinsch et al. | |
| 2012/0277286 A1 | 11/2012 | Youle et al. | |
| 2014/0011890 A1 | 1/2014 | Milbrandt et al. | |
| 2014/0065099 A1 | 3/2014 | Alvarez et al. | |
| 2014/0142121 A1 | 5/2014 | Altieri et al. | |
| 2015/0132760 A1 | 5/2015 | Vance et al. | |
| 2015/0168379 A1 | 6/2015 | Luo et al. | |
| 2016/0030517 A1 | 2/2016 | Morrison et al. | |
| 2016/0213643 A1 | 7/2016 | Rinsch et al. | |
| 2017/0027957 A1 | 2/2017 | Fernyhough et al. | |
| 2017/0180276 A1 | 6/2017 | Gershony et al. | |
| 2017/0274046 A1 | 9/2017 | Morrison et al. | |
| 2018/0015057 A1 | 1/2018 | Evans et al. | |
| 2018/0015098 A1 | 1/2018 | Lichenstein et al. | |
| 2018/0028520 A1 | 2/2018 | Henderson et al. | |
| 2018/0080926 A1 | 3/2018 | Mochly-Rosen et al. | |
| 2018/0082926 A1 | 3/2018 | Campbell et al. | |
| 2018/0085391 A1 | 3/2018 | Bouchon et al. | |
| 2018/0147252 A1 | 5/2018 | Mochly-Rosen et al. | |
| 2018/0305328 A1 | 10/2018 | Beyrath et al. | |
| 2018/0371007 A1 | 12/2018 | Moghadam | |
| 2019/0086429 A1 | 3/2019 | Nagele | |
| 2019/0091291 A1 | 3/2019 | Sue et al. | |
| 2019/0169158 A1 | 6/2019 | Springer et al. | |
| 2019/0204342 A1 | 7/2019 | Canto Alvarez et al. | |
| 2019/0262308 A1 | 8/2019 | Kolliputi et al. | |
| 2019/0328758 A1 | 10/2019 | Alvarez et al. | |
| 2019/0374558 A1 | 12/2019 | Reddy et al. | |
| 2020/0054718 A1 | 2/2020 | Milane | |
| 2020/0109136 A1 | 4/2020 | Shi et al. | |
| 2020/0172518 A1 | 6/2020 | Stockley et al. | |
| 2020/0231542 A1 | 7/2020 | Kemp et al. | |
| 2020/0246429 A1 | 8/2020 | Sue et al. | |
| 2020/0261469 A1 | 8/2020 | Gavathiotis et al. | |
| 2020/0281899 A1 | 9/2020 | Dorn, II | |

FOREIGN PATENT DOCUMENTS

| | | |
|---|---|---|
| WO | 2016115632 A1 | 7/2016 |
| WO | 2018013811 A1 | 1/2018 |
| WO | 2018/200323 A1 | 11/2018 |
| WO | 2019067771 A1 | 4/2019 |
| WO | 2019068865 A1 | 4/2019 |
| WO | 2019202162 A1 | 10/2019 |
| WO | 2019229133 A1 | 12/2019 |
| WO | 2019234664 A1 | 12/2019 |
| WO | 2020030954 A1 | 2/2020 |
| WO | 2020112565 A1 | 6/2020 |

OTHER PUBLICATIONS

Cassidy-Stone et al. 'Chemical Inhibition of the Mitochondrial Division Dynamin Reveals Its Role in Bax/Bak-dependent Mitochondrial Outer Membrane Permeabilization', Developmental Cell, 2008, vol. 14, p. 194-195.
PubChem CID: 43476810 Create Date: Jul. 21, 2009 (Jul. 21, 2009) pp. 1-7.
Rocha et al. 'MFN2 agonists reverse mitochondrial defects in preclinical models of Charcot-Marie-Tooth disease type 2A', Science, Apr. 20, 2018, vol. 360, pp. 1-6.
Pubchem-CID; 67977602 Create Date: Nov. 30, 2012 (Nov. 30, 2012) pp. 1-8.
Pubchem-CID: 78971265 Create Date: Oct. 19, 2014 (Oct. 19, 2014) pp. 1-8.
ISRWO of corresponding PCT/US2019/46356 dated Dec. 13, 2019.
ISRWO of corresponding PCT/US2020/14784 dated Apr. 14, 2020.
PubChem CID 3379738, create date: Sep. 8, 2005, 10 pp.
PubChem CID 4219375, create date: Sep. 13, 2005, 11 pp.
PubChem CID 4193377, create date: Sep. 13, 2005, 10 pp.
PubChem CID 109013974, create date: Jan. 15, 2016, 8 pp.
PubChem CID 5051687, create date: Sep. 18, 2005, 8 pp.
PubChem CID 4228546, create date: Sep. 13, 2005, 9 pp.
PubChem CID 1565360, create date: Jul. 11, 2005, 10 pp.
PubChem CID 5051690, create date: Sep. 18, 2005, 9 pp.
PubChem CID 5164287, create date: Sep. 26, 2005, 9 pp.
PubChem CID 249951, create date: Mar. 26, 2005, 9 pp.

* cited by examiner

TRANS-4-HYDROXYCYCLOHEXYL PHENYL AMIDE MITOFUSIN ACTIVATORS AND METHODS OF USE THEREOF

CROSS-REFERENCE TO RELATED APPLICATIONS

The present application is a continuation-in-part of International Patent Application PCT/US2020/014784, filed on Jan. 23, 2020, which claims the benefit of priority under 35 U.S.C. § 119 from U.S. Provisional Patent Applications 62/797,513, filed on Jan. 28, 2019, and 62/949,060, filed on Dec. 17, 2019, each of which is incorporated herein by reference in its entirety.

STATEMENT REGARDING FEDERALLY SPONSORED RESEARCH OR DEVELOPMENT

This invention was made with government support under grants R41NS113642 and R41NS115184 awarded by the National Institutes of Health. The government has certain rights in the invention.

FIELD OF THE INVENTION

Among the various aspects of the present disclosure is the provision of novel active trans-4-hydroxycyclohexyl phenyl amide stereoisomers of small molecule mitofusin activators and methods of use thereof.

The present disclosure generally relates to compositions and methods for treating genetic or acquired central and peripheral neuropathies, neurodegenerative diseases, disorders, or conditions.

SUMMARY

Among the various aspects of the present disclosure is the provision of novel functionally active stereoisomers of small molecule mitofusin activators and methods of use thereof.

One aspect of the present disclosure provides for methods of treating neuropathies, neurodegenerative diseases, disorders, or conditions. In some features, the method comprises administering to a subject a therapeutically effective amount of a composition comprising one or more active stereoisomers of mitofusin activators; the mitofusin activators stimulate mitochondrial fusion and subcellular mitochondrial transport in neurons, thereby evoking resistance to neuronal injury, accelerating neuronal repair, and promoting neuronal regrowth and regeneration.

Another aspect of the present disclosure provides for a method of activating mitofusin in a subject in need thereof. In some features, the method comprises administering to a human subject or affected animal a composition comprising one or more active trans-4-hydroxycyclohexyl stereoisomers of mitofusin activators; the active trans-4-hydroxycyclohexyl stereoisomers of mitofusin activators stimulate mitochondrial fusion and subcellular mitochondrial transport in neurons, thereby evoking resistance to neuronal injury, accelerating neuronal repair, and promoting neuronal regrowth and regeneration; the subject or affected animal has a genetic or acquired central or peripheral neuropathy, neurodegenerative disease, disorder, or condition.

Another aspect of the present disclosure provides for methods of preventing, mitigating, reducing, or enhancing recovery from iatrogenic, traumatic, or collateral nerve damage in a subject in need thereof. In some features, the method comprises administering to a subject a composition comprising one or more active trans-4-hydroxycyclohexyl stereoisomers of mitofusin activators; the active stereoisomers of mitofusin activators stimulate mitochondrial fusion and subcellular mitochondrial transport in neurons, thereby evoking resistance to neuronal injury, accelerating neuronal repair, and promoting neuronal regrowth and regeneration; the subject or affected animal has a genetic or acquired central or peripheral neuropathy, neurodegenerative disease, disorder, or condition.

In some aspects, the active trans-4-hydroxycyclohexyl stereoisomers of mitofusin activators have substantially better functional potency than both 1-[2-(benzylsulfanyl)ethyl]-3-(2-methylcyclohexyl)urea (Cpd A, Rocha Science 2018) and 2-{2-[(5-cyclopropyl-4-phenyl-4H-1,2,4-triazol-3-yl)sulfanyl]propanamido}-4H,5H,6H-cyclopenta[b]thiophene-3-carboxamide (Cpd B, Rocha Science 2018).

In some aspects, the active trans-4-hydroxycyclohexyl stereoisomers of mitofusin activators have substantially better drug-like pharmacokinetic properties than both 1-[2-(benzylsulfanyl)ethyl]-3-(2-methylcyclohexyl)urea (Cpd A, Rocha Science 2018) and 2-{2-[(5-cyclopropyl-4-phenyl-4H-1,2,4-triazol-3-yl)sulfanyl]propanamido}-4H,5H,6H-cyclopenta[b]thiophene-3-carboxamide (Cpd B, Rocha Science 2018).

In some aspects, the active trans-4-hydroxycyclohexyl stereoisomers of mitofusin activators: target mitofusin-1 (MFN1) or mitofusin-2 (MFN2); increase mitochondrial elongation by enhancing mitochondrial fusion; enhance mitochondrial function measured as inner membrane electrochemical polarization; enhance mitochondrial transport in nerve axons; correct cell and organ dysfunction caused by primary or secondary mitochondrial abnormalities; reverse mitochondrial defects (e.g., dysmorphometry, clustering, loss of polarization, loss of motility); restore, activate, regulate, modulate, promote, or enhance the fusion, function, tethering, transport, trafficking (e.g., axonal mitochondrial trafficking), mobility, or movement of mitochondria (in, optionally, a nerve or a neuron); enhance mitochondrial elongation or mitochondrial aspect ratio; disrupt intramolecular restraints in MFN2; allosterically activate MFN2; and repair morphological and functional defects in diseased or damaged neurons with mitochondrial abnormalities.

In some aspects, the active trans-4-hydroxycyclohexyl stereoisomer mitofusin activator comprises one or more compounds having structures represented by formula (I):

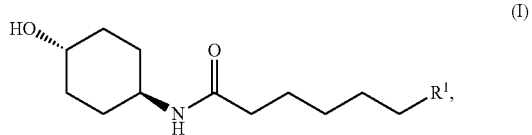

(I)

or a pharmaceutically acceptable salt, tautomer, or stereoisomer thereof wherein, $R^1$ may be a non-, mono-, or poly-substituted $C_{3-8}$ cycloalkyl, $C_{3-8}$ heteroaryl, $C_{3-8}$ aryl, or $C_{3-8}$ heterocyclyl.

In some aspects, the active trans-4-hydroxycyclohexyl stereoisomer mitofusin activator may be a compound having a structure represented by formula (I)

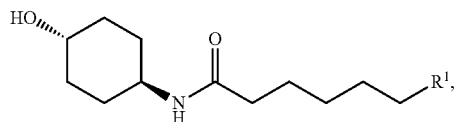

(I)

wherein R¹ may be one of the following moieties:

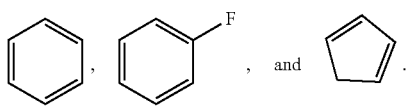

In some aspects, R¹ may be optionally substituted by one or more of: acetamide, $C_{1-8}$ alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene; and optionally further substituted with one or more acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene. Optionally the aforementioned alkyl, cycloalkyl, heteroaryl, heterocyclyl, indole, or phenyl may be further substituted with one or more of the following: acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene.

In some aspects, formula (I) may be one of the following moieties:

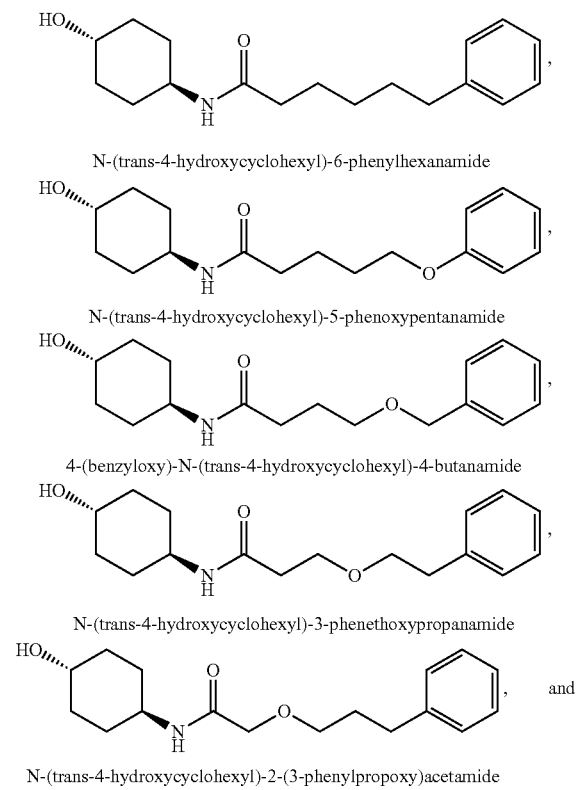

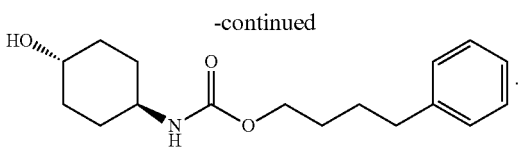

4-phenylbutyl-(trans-4-hydroxycyclohexyl)carbamate

Yet another aspect of the present disclosure provides for a pharmaceutical composition comprising an active trans-4-hydroxycyclohexyl stereoisomer mitofusin activator, optionally in combination with one or more therapeutically acceptable diluents or carriers.

In some aspects, the pharmaceutical composition comprises a pharmaceutically acceptable excipient.

In some aspects, the pharmaceutical composition comprises one or more of the following: neuroprotectants, anti-Parkinsonian drugs, amyloid protein deposition inhibitors, beta amyloid synthesis inhibitors, antidepressants, anxiolytic drugs, antipsychotic drugs, anti-amyotrophic lateral sclerosis drugs, anti-Huntington's drugs, anti-Alzheimer's drugs, anti-epileptic drugs, and/or steroids.

Yet another aspect of the present disclosure provides for a method of treating a mitochondria-associated disease, disorder, or condition in a subject, the method comprising administering to the subject a therapeutically effective amount of a mitofusin activator.

In some aspects, the subject may be diagnosed with or may be suspected of having a mitochondria-associated disease, disorder, or condition.

In some aspects, the mitochondria-associated disease, disorder, or condition may be one or more of: a central nervous system (CNS) or peripheral nervous system (PNS) injury or trauma, such as trauma to the CNS or PNS, crush injury, spinal cord injury (SCI), traumatic brain injury, stroke, optic nerve injury, or related conditions that involve axonal disconnection; a chronic neurodegenerative condition wherein mitochondrial fusion, fitness, or trafficking are impaired; a disease or disorder associated with mitofusin 1 (MFN1) or mitofusin 2 (MFN2) or mitochondrial dysfunction, fragmentation, or fusion; dysfunction in MFN1 or MFN2 unfolding; mitochondria dysfunction caused by mutations; a degenerative neurological condition, such as Alzheimer's disease, Parkinson's disease, Charcot-Marie-Tooth disease, or Huntington's disease; hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, and/or pyruvate dehydrogenase complex deficiency (PDCD/PDH).

Other objects and features will be in part apparent and in part pointed out hereinafter.

DESCRIPTION OF THE DRAWINGS

Those of skill in the art will understand that the drawings, described below are for illustrative purposes only. The drawings are not intended to limit the scope of the present teachings in any way.

FIG. 2A shows the dose-response curves for cis- (Cpd 15A) and trans- (Cpd 15B) MiM 111 stereoisomers in cells expressing only MFN2. FIG. 2B shows the dose-response curves for cis-(Cpd 15A) and trans- (Cpd 15B) MiM 111 stereoisomers in cells expressing only MFN1. "Cpd 2" represents Chimera C, a prototype mitofusin activator for comparison. FIG. 2C shows the FRET analysis of conformational switching provoked by mitofusin activators. Open conformation is more active. "Peptide" is MP1 mitofusin agonist peptide described in reference Franco Nature 2016 and depicted in FIG. 1A.

FIG. 4A shows the total plasma and brain concentrations after single dose IV injections. FIG. 4B shows the steady state elimination kinetics after 3 days of continuous subcutaneous infusion.

FIG. 5A shows the plasma levels after single dose IV (closed circles) or oral (open circles) administration. FIG. 5B shows kymographs demonstrating mitochondrial motility in sciatic nerves of CMT2A mice 6 hours after oral administration as in A. Motile mitochondria exhibit horizontal displacement (corresponding group quantitative data are on the right).

DETAILED DESCRIPTION

The present disclosure is based, at least in part, on the discovery that pharmacophore modeling of function-critical MFN2-derived interacting peptides may produce structurally diverse small molecule peptidomimetic activators useful to treat mitochondrial-associated diseases, disorders, and conditions. As shown herein, the present disclosure provides stereoisomer-specific chemicals or compositions for regulating mitochondrial function. These compositions may be useful to correct organelle, cell, and organ dysfunction caused by primary or secondary mitochondrial abnormalities that cause or contribute to disease pathology and dysfunction.

Mitofusin Activators

The present disclosure provides for a class of stereoisomer-specific trans-4-hydroxycyclohexyl derivative small molecules that promote a change in configuration of MFN1 and MFN2 leading to heightened activation. As described herein, a composition for the treatment of a mitochondria-associated disease, disorder, or condition may comprise an active trans-4-hydroxycyclohexyl mitofusin activator, such as a peptidomimetic (e.g., a small-molecule that mimics the chemico-structural features of a peptide). A peptidomimetic may be a chemical peptidomimetic. For example, the peptidomimetic may mimic a mitofusin-derived mini-peptide. Certain metabolites of the mitofusin activator may also maintain activity in vivo.

Figure 1A:
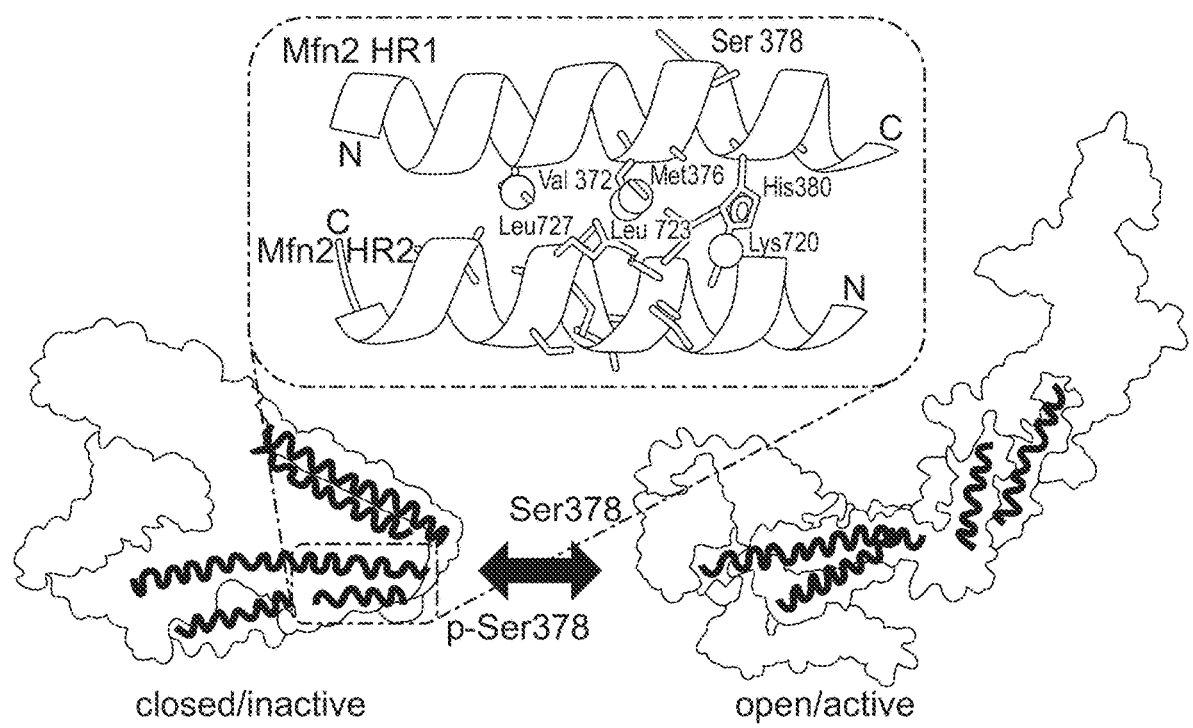
FIG. 1A illustrates a structural model of human MFN2 in the closed/inactive (left) and open/active conformation (right) that may be promoted by mitofusin activators.
Figure 1B:
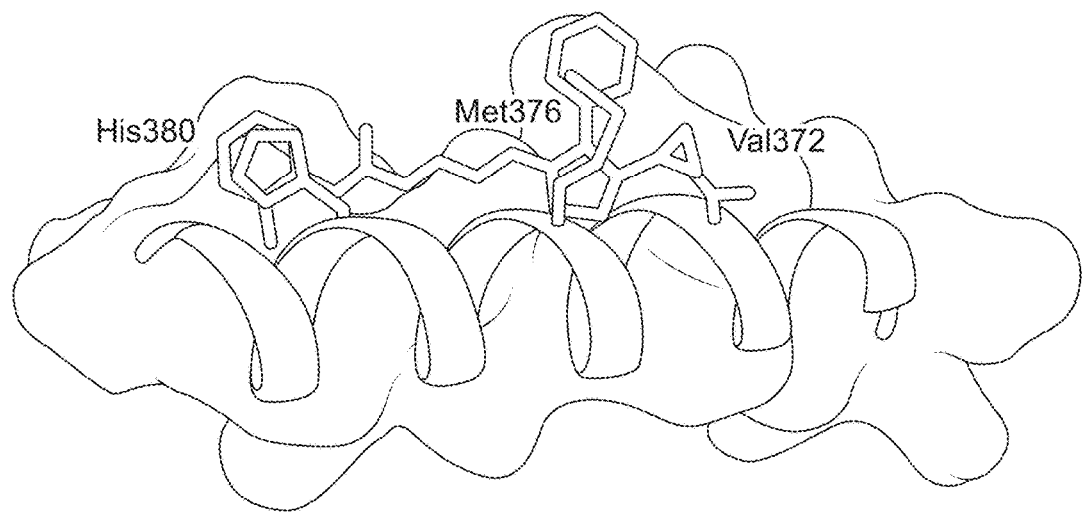
FIG. 1B depicts a pharmacophore modeling of interacting amino acid side chains that resulted in the prototype mitofusin small molecule agonist (Rocha, et al.; Science 2018).
Figure 2A:
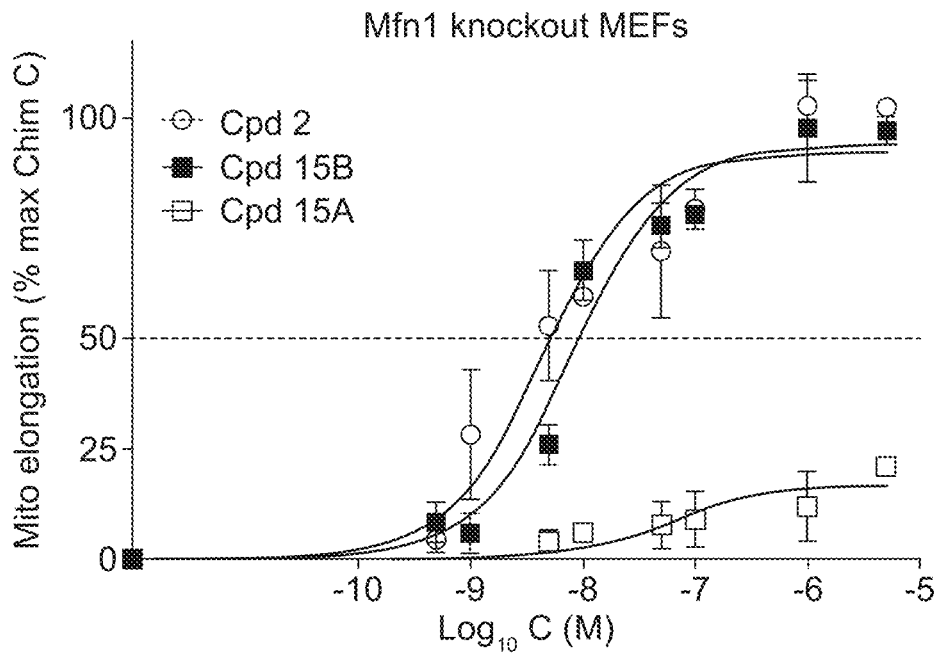
FIGS. 2A-2C depict structure-function relationships of MiM 111 cis- and trans-isostereomers (see e.g., Example 3).
Figure 2B:
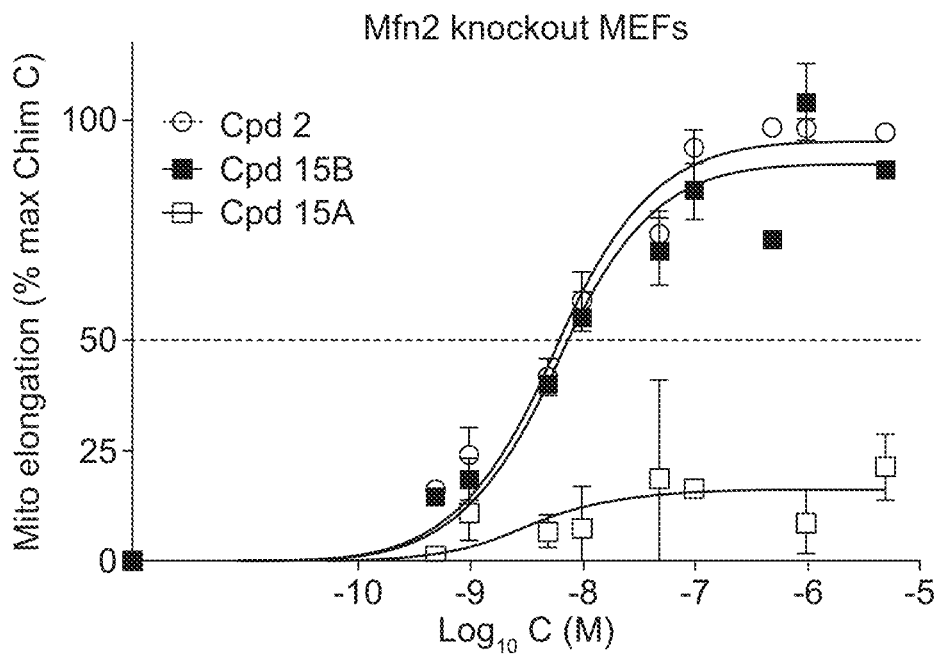
Figure 2C:
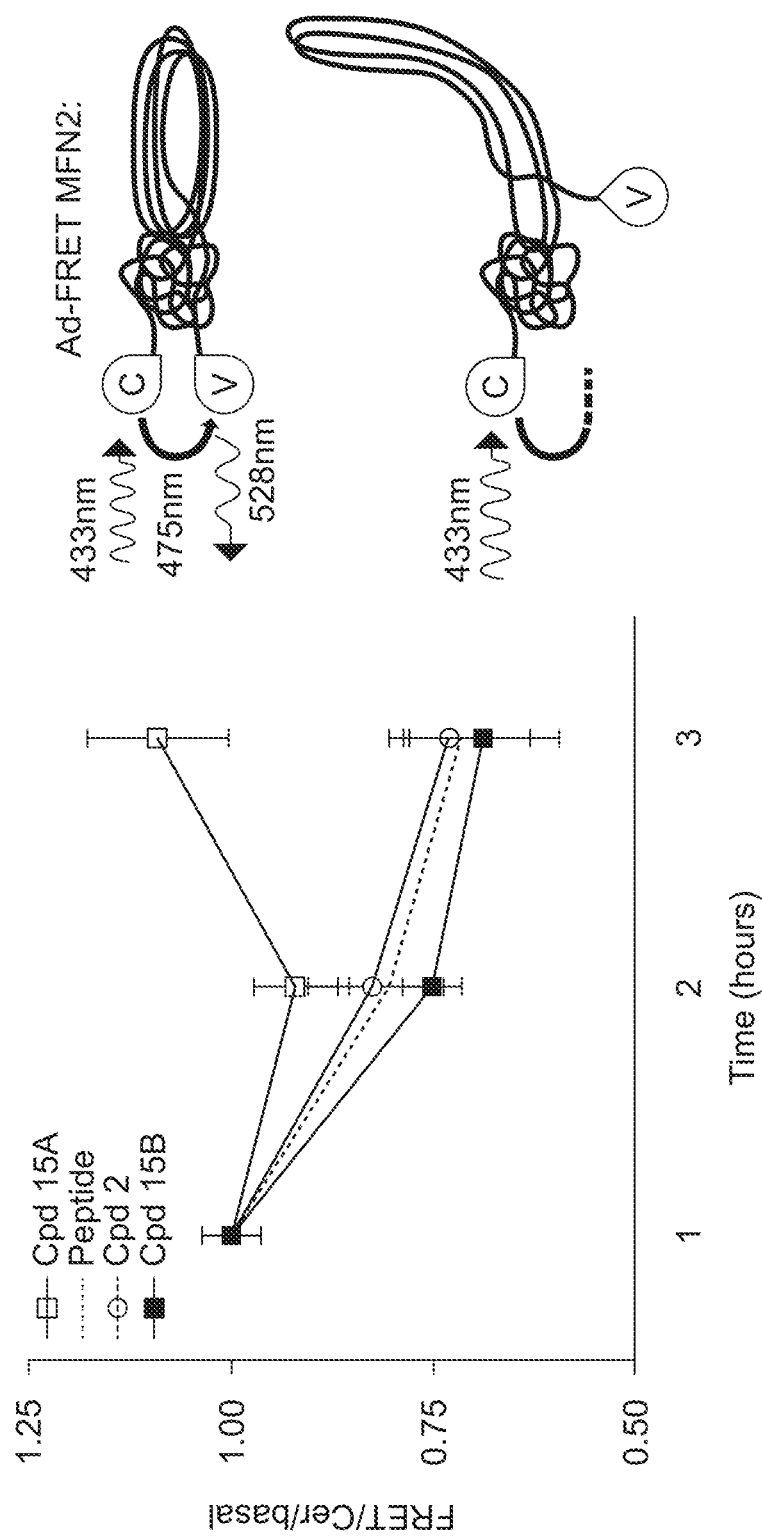

The present disclosure describes functional activity of small molecule peptidomimetics requiring mimicry of the endogenous peptide conformation in 3-dimensional space. Diastereomers of the same chemical mitofusin activator prefer different 3-dimensional structures (FIGS. 1A-1B). Thus, cis- and trans-4-hydroxycyclohexyl derivatives exhibit dramatically different abilities to physically engage with and functionally activate their mitofusin protein targets (FIG. 2A-2C).

As described herein, a new generation of trans-4-hydroxycyclohexyl derivative peptidomimetic small molecules has been developed exhibiting stereoisomer-specific functional activity. These compounds activate mitochondrial fusion by directing MFN1 and MFN2 to different conformational states. The prototype small molecule peptidomimetics to target MFN1 or MFN2 (described in Rocha, et al.; Science, 2018) had poor pharmacokinetic characteristics, making them "undruggable." Described herein are active stereoisomers of a structurally distinct class of small molecule mitofusin activators that activate mitochondrial fusion and subcellular transport, have favorable pharmacokinetic properties, and may be used to correct mitochondrial and cellular dysfunction.

Mitofusin Mini-Peptide

As described herein, a peptide mitofusin activator may be an MFN2-derived mini-peptide as described in Franco, et al.; Nature 2016.

MFN Activator (Fusion-Promoting) Peptidomimetic

As described herein, a peptidomimetic may be a MFN activator (fusion-promoting) peptidomimetic that competes with endogenous MFN1 or MFN2 HR1-HR2 peptide-peptide interactions as described in Franco, et al.; *Nature* 2016 and Rocha, et al.; *Science* 2018.

The prototype mitofusin activator, Chimera C according to the present disclosure, includes the following compound:

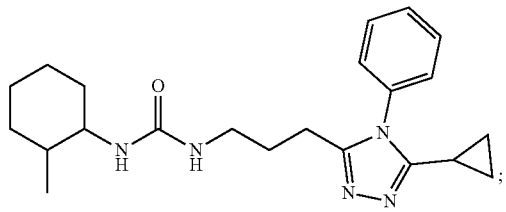

1-(3-(5-cyclopropyl-4-phenyl-4H-1,2,4-triazol-3-yl)propyl)-3-(2-methylcyclohexyl)urea (Chimera-C, M.W.: 381.52 g/mol, Formula: $C_{22}H_{31}N_5O$)

Mitofusin Activators: Structurally Distinct Small Molecules that Activate MFN1 and/or MFN2

The small molecule mitofusin activators described herein are allosteric mitofusin activators designed in part using the pharmacophore HR1-HR2 peptide-peptide interaction model described in Rocha, et al.; *Science* 2018, but which are structurally distinct and of separate chemical classes from those reported by Rocha. An activator is a substance that partially or fully activates the protein to which it binds.

The mitofusin activator may comprise one or more compounds represented by formula (I):

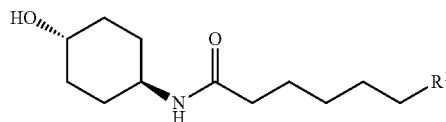

(I)

or a pharmaceutically acceptable salt, tautomer, or stereoisomer thereof, wherein $R^1$ may be selected from the following moieties:

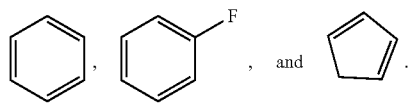

Optionally, $R^1$ in formula (I) may be independently substituted by one or more of the following groups: acetamide, $C_{1-8}$ alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene and optionally further substituted with acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene and the alkyl, cycloalkyl, heteroaryl, heterocyclyl, indole, or phenyl may be optionally further substituted with one or more of the following groups: acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone and/or thiophene.

Optionally, the $R^1$ group in formula (I) may be independently substituted with one or more of the following groups: hydroxyl; $C_{1-10}$ alkyl hydroxyl (i.e., $C_1$-$C_{10}$ alkoxides); amine; $C_{1-10}$ carboxylic acid; $C_{1-10}$ carboxyl; straight chain or branched $C_{1-10}$ alkyl, optionally containing unsaturation; a $C_{2-8}$ cycloalkyl optionally containing unsaturation or one oxygen or nitrogen atom; straight chain or branched $C_{1-10}$ alkyl amine; heterocyclyl; heterocyclic amine; and/or aryl comprising phenyl, heteroaryl containing from one to four of the following heteroatoms: N, O, and/or S, unsubstituted phenyl ring, substituted phenyl ring, unsubstituted heterocyclyl, and substituted heterocyclyl. Optionally, the unsubstituted phenyl ring or substituted phenyl ring may be independently substituted with one or more of the following groups: hydroxyl; $C_{1-10}$ alkyl hydroxyl (i.e., $C_1$-$C_{10}$ alkoxides); amine; $C_{1-10}$ carboxylic acid; $C_{1-10}$ carboxyl; straight chain or branched $C_{1-10}$ alkyl, optionally containing unsaturation; straight chain or branched $C_{1-10}$ alkyl amine, optionally containing unsaturation; a $C_{2-10}$ cycloalkyl optionally containing unsaturation or one oxygen or nitrogen atom; straight chain or branched $C_{1-10}$ alkyl amine; heterocyclyl; heterocyclic amine; and/or aryl comprising phenyl and heteroaryl containing from one to four of the following heteroatoms: N, O, and/or S. Optionally, the unsubstituted heterocyclyl or substituted heterocyclyl may be independently substituted with one or more of the following groups: hydroxyl; $C_{1-10}$ alkyl hydroxyl (i.e., $C_1$-$C_{10}$ alkoxides); amine; $C_{1-10}$ carboxylic acid; $C_{1-10}$ carboxyl; straight chain or branched $C_{1-10}$ alkyl optionally containing unsaturation; straight chain or branched $C_{1-10}$ alkyl amine optionally containing unsaturation; a $C_{2-8}$ cycloalkyl optionally containing unsaturation or one oxygen or nitrogen atom; heterocyclyl; straight chain or branched $C_{1-10}$ alkyl amine; heterocyclic amine; and/or aryl comprising a phenyl and a heteroaryl containing from one to four of the following heteroatoms: N, O, and S. Any of the above may be further optionally substituted.

In some aspects, $R^1$ in formula (I) may be optionally substituted by one or more of the following groups: acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene; and optionally further substituted with one or more of the following groups: acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, or thiophene; wherein the alkyl, cycloalkyl, heteroaryl, heterocyclyl, indole, or phenyl, may be optionally further substituted with one or more of acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene.

In another aspect of the disclosure, the mitofusin activator may comprise one or more compounds represented by formula (II):

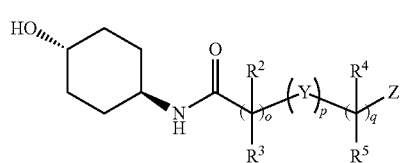

(II)

or a pharmaceutically acceptable salt thereof. In Formula (II), o may be 0, 1, 2, 3, 4, or 5; p may be 0 or 1; and q may be 0, 1, 2, 3, 4, or 5 with the proviso that the sum of o+p+q is not less than 3 or greater than 7; Z may be cycloalkyl, heterocycloalkyl, aryl, or heteroaryl; $R^2$ and $R^3$ may be independently H, F, alkyl, or $C_{3-7}$ cycloalkyl; or optionally, $R^2$ and $R^3$ taken together may form a $C_{3-7}$ cycloalkyl or heterocycloalkyl; $R^4$ and $R^5$ may be independently H, F, alkyl, $COR^8$, or $C_{3-7}$ cycloalkyl; or optionally, $R^4$ and $R^5$ taken together may form a $C_{3-7}$ cycloalkyl or heterocycloalkyl; Y may be O, $CR^6R^7$, $CR^8$=$CR^9$, C≡C, cycloalkyl, heterocycloalkyl, aryl, heteroaryl, $NR^8$, S, $SO_2$, $SONR^9$, $NR^9SO_2$, $NR^8CO$, $CONR^8$, $NR^7CONR^9$; each $R^6$ may be independently selected from H, alkyl, and $C_{3-7}$ cycloalkyl; each $R^7$ may be independently selected from H, alkyl, $COR^8$ and $C_{3-7}$ cycloalkyl; or optionally, $R^6$ and $R^7$ taken together may form $C_{3-7}$ cycloalkyl; and each $R^8$ may be independently selected from H, alkyl, and $C_{3-7}$ cycloalkyl; each $R^9$ may be independently selected from H, alkyl, $COR^8$ and $C_{3-7}$ cycloalkyl; or optionally, $R^8$ and $R^9$ may be taken together to form $C_{3-7}$ cycloalkyl.

In some aspects, in the mitofusin activator of formula (II), o may be 0, 1, 2, 3, 4, or 5; p may be 0 or 1; and q may be 0, 1, 2, 3, 4, or 5 with the proviso that the sum of o+p+q is not less than 3 or greater than 7; Z may be cycloalkyl, heterocycloalkyl, aryl, or heteroaryl; Y may be O, $CR^6R^7$, cycloalkyl, or aryl; and $R^2$, $R^3$, $R^4$, $R^5$, $R^6$ and $R^7$ may be independently selected from H or alkyl.

In some aspects, in the mitofusin activator of formula (II), o may be 0, 1, 2, 3, 4, or 5; p may be 0 or 1; and q may be 0, 1, 2, 3, 4, or 5 with the proviso that the sum of o+p+q is not less than 3 or greater than 5; Z may be aryl or heteroaryl; Y may be O, CH$_2$, or cycloalkyl; R$^2$, R$^3$, R$^4$ and R$^5$ may each be H.

In some aspects, in the mitofusin activator of formula (II), o may be 0, 1, 2, or 3; p may be 1; and q may be 0, 1, 2, or 3 with the proviso that the sum of o+p+q is not less than 3 or greater than 5; Z may be aryl or heteroaryl; Y may be cyclopropyl or cyclobutyl; R$^2$, R$^3$, R$^4$ and R$^5$ may each be H.

In some aspects, in the mitofusin activator of formula (II), Z may be aryl or heteroaryl; Y may be O or CH$_2$, R$^2$, R$^3$, R$^4$ and R$^5$ may each be H; o may be 0, 1, 2, 3, or 4; p may be 1; and q may be 0, 1, 2, 3, or 4 with the proviso that the sum of o+p+q is 5.

In some aspects, in the mitofusin activator of formula (II), Z may be phenyl or heteroaryl, wherein the heteroaryl may contain from one to four heteroatoms independently selected from N, O, and S, and wherein the phenyl or heteroaryl may be substituted with zero to four of the following independently-chosen substituents: R$^8$, OR$^8$, Cl, F, CN, CF$_3$, NR$^8$R$^9$, SO$_2$NR$^8$R$^9$, NR$^8$SO$_2$R$^{10}$, SO$_2$R$^9$, CONR$^8$R$^{10}$, NR$^8$COR$^{10}$, C$_{3-7}$ cycloalkyl, and/or heterocycloalkyl; each R$^8$ may be independently selected from H, alkyl, and C$_{3-7}$ cycloalkyl; each R$^9$ may be independently selected from H, alkyl, COR$^7$ and C$_{3-7}$ cycloalkyl; or optionally, R$^8$ and R$^9$ taken together may form a C$_{3-7}$ cycloalkyl; Y may be O or CH$_2$, R$^2$, R$^3$, R$^4$, and R$^5$ may each be H; o may be 0, 1, 2, 3, or 4; p may be 1; and q may be 0, 1, 2, 3, or 4 with the proviso that the sum of o+p+q is 5.

In some aspects, in the mitofusin activator of formula (II), Z may be phenyl or heteroaryl, wherein the heteroaryl may contain one to three of the following heteroatoms: N, O, and S, and wherein the phenyl or heteroaryl may contain zero to three of the following substituents independently selected from R$^8$, OR$^8$, Cl, F, CN, CF$_3$, NR$^8$R$^9$, SO$_2$R$^9$, CONR$^8$R$^{10}$, NR$^8$COR$^{10}$, C$_{3-7}$ cycloalkyl, and/or heterocycloalkyl; Y may be O or CH$_2$, R$^2$, R$^3$, R$^4$, and R$^5$ may each be H; each R$^8$ may independently be selected from H, alkyl, and C$_{3-7}$ cycloalkyl; each R$^9$ may be independently selected from H, alkyl, COR$^7$ and C$_{3-7}$ cycloalkyl; or optionally, R$^8$ and R$^9$ taken together may form a C$_{3-7}$ cycloalkyl; each R$^9$ may be alkyl or C$_{3-7}$ cycloalkyl; o may be 0, 1, 2, 3, or 4; p may be 1; and q may be 0, 1, 2, 3, or 4 with the proviso that the sum of o+p+q is 5.

In some aspects, in the mitofusin activator of formula (II), Z may be phenyl, 2-pyridinyl, 3-pyridinyl, 4-pyridinyl, 6-pyrimidinyl, 5-pyrimidinyl, 4-pyrimidinyl, or 2-pyrimidinyl, wherein the phenyl, pyridinyl, and pyrimidinyl moieties may independently contain zero to two of the following independently-chosen substituents: R$^8$, OR$^8$, Cl, F, CN, CF$_3$, NR$^8$R$^9$, SO$_2$R$^9$, CONR$^8$R$^9$, and/or NR$^8$COR$^{10}$; Y may be O or CH$_2$, R$^2$, R$^3$, R$^4$, and R$^5$ may each be H; each R$^8$ may independently be H, alkyl, and C$_{3-7}$ cycloalkyl; each R$^9$ may be independently selected from H, alkyl, COR$^7$ and C$_{3-7}$ cycloalkyl; or optionally, R$^8$ and R$^9$ taken together may form a C$_{3-7}$ cycloalkyl; R$^{10}$ may be alkyl or C$_{3-7}$ cycloalkyl; o may be 0, 1, 2, 3, or 4; p may be 1; and q may be 0, 1, 2, 3, or 4 with the proviso that the sum of o+p+q is 5.

Accordingly, in some aspects, in the mitofusin activator of formula (II), Z may be cycloalkyl, heterocycloalkyl, aryl, or heteroaryl; R$^2$ and R$^3$ may be independently selected from H, F, alkyl, and C$_{3-7}$ cycloalkyl, or R$^2$ and R$^3$ taken together may form a C$_{3-7}$ cycloalkyl or heterocycloalkyl; R$^4$ and R$^5$ may be independently selected from H, F, alkyl, and C$_{3-7}$ cycloalkyl, or R$^4$ and R$^5$ taken together may form a C$_{3-7}$ cycloalkyl or heterocycloalkyl; Y is O, CR$^6$R$^7$; CR$^8$CR$^9$, C≡C, cycloalkyl, heterocycloalkyl, aryl, heteroaryl, NR$^8$, S, SO$_2$, SONR$^9$, NR$^9$SO$_2$, NR$^8$CO, CONR$^8$, or NR$^8$CONR$^9$; R$^6$ may be H, F, alkyl or cycloalkyl; R$^7$ may be H, F, alkyl or cycloalkyl; or R$^6$ and R$^7$ taken together may form a C$_{3-7}$ cycloalkyl or heterocycloalkyl; R$^8$ may be H, F, alkyl or cycloalkyl; R$^9$ may be H, F, alkyl or cycloalkyl; or R$^8$ and R$^9$ taken together may form a C$_{3-7}$ cycloalkyl; o is 0, 1, 2, 3, 4, or 5; p is 0 or 1; and q is 0, 1, 2, 3, 4, or 5, provided that if Y is cycloalkyl, particularly cyclopropyl or cyclobutyl, the sum of o+p+q is not less than 3 or greater than 5, and otherwise the sum of o+p+q is 5.

In particular aspects, in the mitofusin activator of formula (II), Z may be aryl or heteroaryl; Y may be O, CR$^6$R$^7$, or cycloalkyl; R$^2$, R$^3$, R$^4$, R$^5$, R$^6$, and R$^7$ may be H or alkyl; and p is 1. In other particular aspects, Y may be cyclopropyl or cyclobutyl, or Y may be O or CH$_2$, R$^2$, R$^3$, R$^4$, and R$^5$ may each be H; and p is 1. In still other particular aspects, Z may be phenyl or heteroaryl, wherein the heteroaryl is 2-pyridinyl, 3-pyridinyl, 4-pyridinyl, 2-pyrimidinyl, 4-pyrimidinyl, 5-pyrimidinyl, or 6-pyrimidinyl, wherein the phenyl or heteroaryl may be optionally substituted. Optional substitutions include 0 to 4, or 0 to 3, or 0 to 2 substituents independently selected from R$^8$, OR$^8$, Cl, F, CN, CF$_3$, NR$_8$R$_9$, SO$_2$NR$_8$R$_9$, NR$_8$SO$_2$R$_9$, SO$_2$R$_9$, CONR$_8$R$_9$, NR$_8$COR$_{10}$, C$_{3-7}$ cycloalkyl, and heterocycloalkyl.

Mitofusin activators of the present disclosure may stimulate mitochondrial fusion, increase mitochondrial fitness, and enhance mitochondrial subcellular transport. More particular examples of mitofusin activators suitable for achieving one or more of these results may include trans-stereoisomers of 6-phenylhexanamide derivatives or a pharmaceutically acceptable salt thereof, particularly 6-phenyl hexanamide derivatives that are N-substituted with a trans-4-cyclohexyl group. Compositions of the present disclosure and methods employing comprising trans-stereoisomers of 6-phenylhexanamide derivatives may contain greater than a 1:1 molar ratio of the trans-stereoisomer relative to the cis-stereoisomer, such as at least about 60% or greater trans-stereoisomer on a molar basis, or about 70% or greater, or about 80% or greater, or about 90% or greater, or about 95% or greater, or about 97% or greater, or about 99% or greater. Compositions may even comprise trans-stereoisomer 6-phenylhexanamide derivatives that are racemically pure.

Particular examples of trans-stereoisomer 6-phenylhexanamide derivatives having activity for promoting mitofusin activation include, for example,

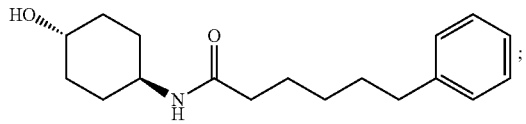

N-(trans-4-hydroxycyclohexyl)-6-phenylhexanamide

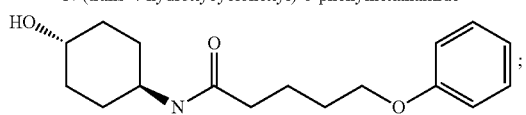

N-(trans-4-hydroxycyclohexyl)-5-phenoxypentanamide

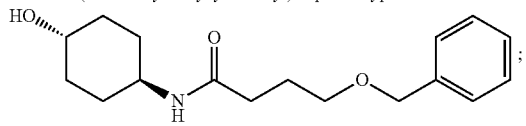

4-(benzyloxy)-N-(trans-4-hydroxycyclohexyl)-4-butanamide

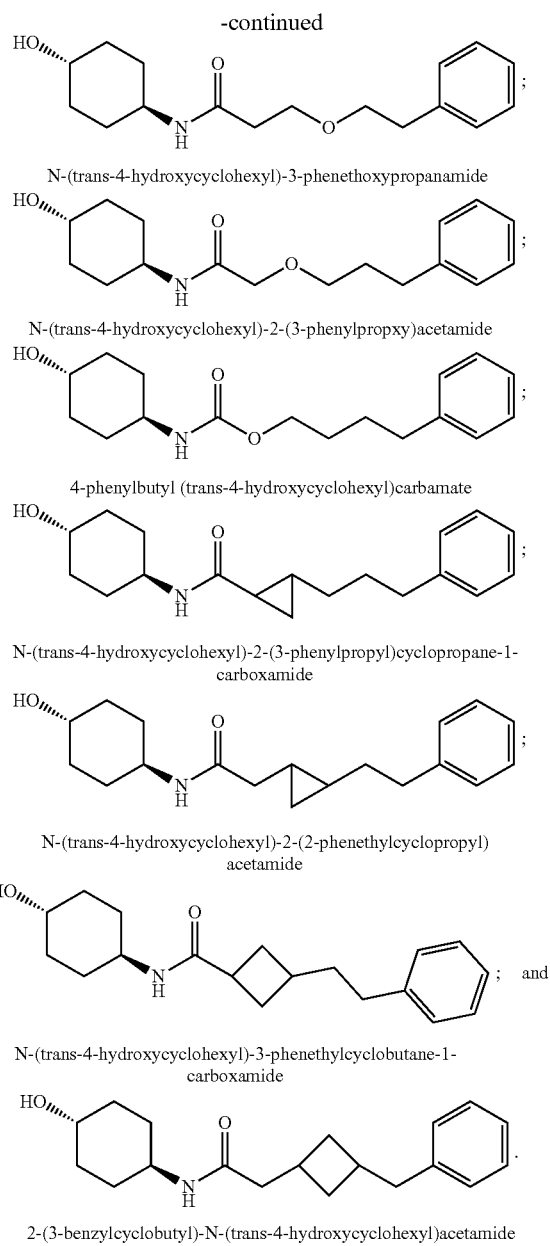

N-(trans-4-hydroxycyclohexyl)-3-phenethoxypropanamide

N-(trans-4-hydroxycyclohexyl)-2-(3-phenylpropxy)acetamide 4-phenylbutyl (trans-4-hydroxycyclohexyl)carbamate N-(trans-4-hydroxycyclohexyl)-2-(3-phenylpropyl)cyclopropane-1-carboxamide N-(trans-4-hydroxycyclohexyl)-2-(2-phenethylcyclopropyl)acetamide N-(trans-4-hydroxycyclohexyl)-3-phenethylcyclobutane-1-carboxamide ; and 2-(3-benzylcyclobutyl)-N-(trans-4-hydroxycyclohexyl)acetamide In another aspect of the present disclosure, a method of treating a disease for which a mitofusin activator is indicated may comprise administering to a mammal in need thereof, such as a human, a therapeutically effective amount of a compound of formula (II)

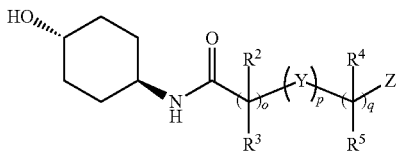

(II)

or a pharmaceutically acceptable salt thereof. In Formula (II), o may be 0, 1, 2, 3, 4, or 5; p may be 0 or 1; and q may be 0, 1, 2, 3, 4, or 5 with the proviso that the sum of o+p+q is not less than 3 or greater than 7; Z may be cycloalkyl, heterocycloalkyl, aryl, or heteroaryl; $R^2$ and $R^3$ may be independently H, F, alkyl, or $C_{3-7}$ cycloalkyl; or optionally, $R^2$ and $R^3$ taken together may form a $C_{3-7}$ cycloalkyl or heterocycloalkyl; $R^4$ and $R^5$ may be independently H, F, alkyl, $COR^8$, or $C_{3-7}$ cycloalkyl; or optionally, $R^4$ and $R^5$ taken together may form a $C_{3-7}$ cycloalkyl or heterocycloalkyl; Y may be O, $CR^6R^7$, $CR^8$=$CR^9$, C≡C, cycloalkyl, heterocycloalkyl, aryl, heteroaryl, $NR^8$, S, $SO_2$, $SONR^9$, $NR^9SO_2$, $NR^8CO$, $CONR^8$, $NR^7CONR^9$; each $R^6$ may be independently selected from H, alkyl, and $C_{3-7}$ cycloalkyl; each $R^7$ may be independently selected from H, alkyl, $COR^8$ and $C_{3-7}$ cycloalkyl; or optionally, $R^6$ and $R^7$ taken together may form $C_{3-7}$ cycloalkyl; and each $R^8$ may be independently selected from H, alkyl, and $C_{3-7}$ cycloalkyl; each $R^9$ may be independently selected from H, alkyl, $COR^8$ and $C_{3-7}$ cycloalkyl; or optionally, $R^8$ and $R^9$ may be taken together to form $C_{3-7}$ cycloalkyl. Any of the mitofusin activators specified above may be employed for treating a human or other mammal having or suspected of having a mitochondria-associated disease, disorder or condition.

The mitochondria-associated disease, disorder or condition may be a pheripheral nervous system (PNS) or central nervous system (CNS) genetic or non-genetic disorder, physical damage, and/or chemical injury. In some aspects, in the method of treating a disease for which a mitofusin activator is indicated, the PNS or CNS disorder may be selected from any one or a combination of: a chronic neurodegenerative condition wherein mitochondrial fusion, fitness, or trafficking are impaired; a disease or disorder associated with mitofusin-1 (MFN1) or mitofusin-2 (MFN2) dysfunction; a disease associated with mitochondrial fragmentation, dysfunction, or dysmotility; a degenerative neuromuscular condition such as Charcot-Marie-Tooth disease, amyotrophic lateral sclerosis (ALS), Huntington's disease, Alzheimer's disease, Parkinson's disease, hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, or pyruvate dehydrogenase complex deficiency (PDCD/PDH), diabetic neuropathy, chemotherapy-induced peripheral neuropathy, crush injury, SCI, traumatic brain injury (TBI), stroke, optic nerve injury, and/or related conditions that involve axonal disconnection.

In some aspects of the disclosure, in the method of treating a disease for which a mitofusin activator is indicated, the composition may further comprise a pharmaceutically acceptable excipient.

In some aspects of the disclosure, in the method of treating a CNS and/or PNS genetic and/or non-genetic neurodegenerative condition, injury, damage, and/or trauma comprising administering to the subject a therapeutically effective amount of a mitofusin activator according to the present disclosure.

In some aspects of the disclosure, in the method of treating a CNS or PNS genetic or non-genetic neurodegenerative condition, injury, damage, or trauma, the subject may be diagnosed with or may be suspected of having one or more of the following: a chronic neurodegenerative condition wherein mitochondrial fusion, fitness, or trafficking are impaired; a disease or disorder associated with MFN1 or MFN2 dysfunction; a disease associated with mitochondrial fragmentation, dysfunction, or dysmotility; a degenerative neuromuscular condition (such as Charcot-Marie-Tooth disease, ALS, Huntington's disease, Alzheimer's disease, Parkinson's disease); hereditary motor and sensory neuropathy, autism, ADOA, muscular dystrophy, Lou Gehrig's disease, cancer, mitochondrial myopathy, DAD, LHON, Leigh syndrome, subacute sclerosing encephalopathy, NARP, MNGIE, MERRF, MELAS, mtDNA depletion, MNGIE, dysautonomic mitochondrial myopathy, mitochondrial Channelopathy, PDCD/PDH, diabetic neuropathy, chemotherapy-induced peripheral neuropathy, crush injury, SCI, TBI, stroke, optic nerve injury, and/or related conditions that involve axonal disconnection.

The terms "imine" or "imino," as used herein, unless otherwise indicated, include a functional group or chemical compound containing a carbon-nitrogen double bond. The expression "imino compound," as used herein, unless otherwise indicated, refers to a compound that includes an "imine" or an "imino" group as defined herein. The "imine" or "imino" group may be optionally substituted.

The term "hydroxy," as used herein, unless otherwise indicated, includes —OH. The "hydroxy" may be optionally substituted (e.g., incorporated in an alkoxide, phenoxide, or carboxylic acid ester).

The terms "halogen" and "halo", as used herein, unless otherwise indicated, include a chlorine, chloro, Cl, fluorine, fluoro, F; bromine, bromo, Br; and iodine, iodo, or I.

The term "acetamide," as used herein, is an organic compound with the formula $CH_3CONH_2$. The "acetamide" may be optionally substituted.

The term "aryl," as used herein, unless otherwise indicated, includes a carbocyclic aromatic group. Examples of aryl groups include, but are not limited to, phenyl, benzyl, naphthyl, and anthracenyl. The "aryl" may be optionally substituted.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group. The "amine" or "amino" group may be optionally substituted.

The term "alkyl," as used herein, unless otherwise indicated, includes saturated monovalent hydrocarbon radicals having straight or branched moieties, such as but not limited to, methyl, ethyl, propyl, butyl, pentyl, hexyl, and octyl groups. Representative straight-chain lower alkyl groups include, but are not limited to, methyl, ethyl, n-propyl, n-butyl, n-pentyl, n-hexyl, n-heptyl and n-octyl. Branched lower alkyl groups include, but are not limited to, isopropyl, sec-butyl, isobutyl, tert-butyl, isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 1-hexyl, 2-hexyl, 3-hexyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, and 3-methylheptyl. Unsaturated alkyl groups may be referred to as alkenyl (at least one carbon-carbon double bond) or alkynyl (at least one carbon-carbon triple bond) groups, which may include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, acetylenyl, propynyl, -1-butynyl, 2-butynyl, 1-pentynyl, 2-pentynyl, or 3-methyl-1 butynyl. E and Z isomers may be present in any alkenyl group. The "alkyl," "alkenyl," or "alkynyl" may be optionally substituted.

The term "carboxyl," as used herein, unless otherwise indicated, includes a functional group containing a carbon atom double bonded to an oxygen atom and single bonded to a hydroxyl group (—COOH). The "carboxyl" may be optionally substituted.

The term "acyl," as used herein, unless otherwise indicated, includes a functional group derived from an aliphatic carboxylic acid by removal of the hydroxyl (—OH) group. The "acyl" may be optionally substituted.

The term "alkoxy," as used herein, unless otherwise indicated, includes O-alkyl groups wherein alkyl is as defined above and O represents oxygen. Representative alkoxy groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2,4dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl, —O-3-methyl-1-butynyl, —O-cyclopropyl, —O-cyclobutyl, —O-cyclopentyl, —O-cyclohexyl, —O-cycloheptyl, —O-cyclooctyl, —O-cyclononyl, —O-cyclodecyl, cyclodecyl, —O—$CH_2$-cyclopropyl, —O—$CH_2$-cyclobutyl, —O—$CH_2$-cyclopentyl, —O—$CH_2$-cyclohexyl, —O—$CH_2$-cycloheptyl, —O—$CH_2$-cyclooctyl, —O—$CH_2$-cyclononyl, —O—$CH_2$-cyclodecyl, —O—$(CH_2)_n$-cyclopropyl, —O—$(CH_2)_n$-cyclobutyl, —O—$(CH_2)_n$-cyclopentyl, —O—$(CH_2)_n$-cyclohexyl, —O—$(CH_2)_n$-cycloheptyl, —O—$(CH_2)_n$-cyclooctyl, —O—$(CH_2)_n$-cyclononyl, and/or —O—$(CH_2)_n$-cyclodecyl. The alkoxy may be saturated, partially saturated, or unsaturated. The "alkoxy" may be optionally substituted. In any example above, n may be from one to about twenty.

The term "cycloalkyl," as used herein, unless otherwise indicated, includes a non-aromatic, saturated, partially saturated, or unsaturated, monocyclic or fused, spiro or unfused bicyclic or tricyclic hydrocarbon referred to herein containing a total of from 3 to 10 carbon atoms. Examples of cycloalkyls include, but are not limited to, $C_{3-10}$ cycloalkyl groups including cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl. The term "cycloalkyl" also includes lower alkyl-cycloalkyl, wherein lower alkyl and cycloalkyl are as defined herein. Examples of -lower alkyl-cycloalkyl groups include, but are not limited to, —$CH_2$-cyclopropyl, —$CH_2$-cyclobutyl, —$CH_2$-cyclopentyl, —$CH_2$-cyclopentadienyl, —$CH_2$-cyclohexyl, —$CH_2$-cycloheptyl, and/or —$CH_2$-cyclooctyl. The "cycloalkyl" may be optionally substituted.

The term "heterocyclic" as used herein, unless otherwise indicated, includes an aromatic group or non-aromatic cycloalkyl group in which one to four of the ring carbon atoms are independently replaced with one or more of O, S, and N. Aromatic heterocyclic groups are referred to as "heteroaryl" groups. Non-aromatic heterocyclic groups are referred to as "heterocyclyl" groups. Representative examples of heterocyclic groups include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, and/or tetrazolyl. Heterocyclic groups may be substituted or unsubstituted. Heterocyclic groups may also be bonded at any ring atom (i.e., at any carbon atom or heteroatom of the heterocyclic ring). The heterocyclic group may be saturated, partially saturated, or unsaturated.

The term "indole," as used herein, is an aromatic heterocyclic organic compound with formula $C_8H_7N$. It has a bicyclic structure containing a six-membered benzene ring fused to a five-membered nitrogen-containing pyrrole ring. The "indole" may be optionally substituted.

The term "cyano," as used herein, unless otherwise indicated, includes a —CN group.

The term "alcohol," as used herein, unless otherwise indicated, includes a compound in which a hydroxy functional group (—OH) is bound to a carbon atom. In particular, this carbon atom may be saturated, having single bonds to three other atoms. The "alcohol" may be optionally substituted. The "alcohol" may be a primary, secondary, or tertiary alcohol.

The term "solvate" is intended to mean a solvated form of a specified compound that retains the effectiveness of such compound. Examples of solvates include compounds of the invention in combination with, but not limited to, one or more of: water, isopropanol, ethanol, methanol, dimethylsulfoxide (DMSO), ethyl acetate, acetic acid, or ethanolamine.

The term "stereoisomer" encompasses both optical isomers, such as enantiomers or diastereomers, the latter existing due to more than one center of chirality in the molecule, as well as geometrical isomers (cis/trans isomers or diastereomers).

A composition comprising the trans-stereoisomer 6-phenylhexanamide derivative mitofusin activator or a pharmaceutically acceptable salt thereof of the disclosure may comprise the trans-stereoisomer in greater amount than the cis-stereoisomer. A method of using the composition comprising the trans-stereoisomer 6-phenylhexanamide derivative mitofusin activator or a pharmaceutically acceptable salt thereof of the disclosure may be such that the composition comprises the trans-stereoisomer in greater amount than the cis-stereoisomer.

The term "mmol," as used herein, is intended to mean millimole. The term "equiv" and "eq.," as used herein, are intended to mean equivalent. The term "mL," as used herein, is intended to mean milliliter. The term "g," as used herein, is intended to mean gram. The term "kg," as used herein, is intended to mean kilogram. The term "µg," as used herein, is intended to mean micrograms. The term "h," as used herein, is intended to mean hour. The term "min," as used herein, is intended to mean minute. The term "M," as used herein, is intended to mean molar. The term "µL," as used herein, is intended to mean microliter. The term "µM," as used herein, is intended to mean micromolar. The term "nM," as used herein, is intended to mean nanomolar. The term "N," as used herein, is intended to mean normal. The term "amu," as used herein, is intended to mean atomic mass unit. The term "° C.," as used herein, is intended to mean degree Celsius. The term "wt/wt," as used herein, is intended to mean weight/weight. The term "v/v," as used herein, is intended to mean volume/volume. The term "MS," as used herein, is intended to mean mass spectrometry. The term "HPLC," as used herein, is intended to mean high performance liquid chromatography. The term "RT," as used herein, is intended to mean room temperature or retention time, depending on context. The term "e.g.," as used herein, is intended to mean for example. The term "N/A," as used herein, is intended to mean not tested or not applicable.

As used herein, the expression "pharmaceutically acceptable salt" refers to pharmaceutically acceptable organic or inorganic salts of a compound of the invention. Suitable salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and/or pamoate (i.e., 1,1'-methylene-bis-(2-hydroxy-3-naphthoate)) salts. A pharmaceutically acceptable salt may involve the inclusion of another molecule such as an acetate ion, a succinate ion, or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt may have multiple counterions. Hence, a pharmaceutically acceptable salt may have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and/or ethanolamine. As used herein, the expression "pharmaceutically acceptable hydrate" refers to a compound of the invention, or a salt thereof, that further includes a stoichiometric or non-stoichiometric amount of water bound by non-covalent intermolecular forces.

Each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Mitofusin 1 and Mitofusin 2

Mitofusins (MFN) 1 and 2, named for their central roles in mitochondrial fusion, are attractive drug targets because their regulatory functioning in mitochondrial dynamics and quality/quantity control is perturbed in several neurodegenerative disorders. In particular, genetic mutations that abrogate or impair MFN2 functioning and therefore suppress mitochondrial fusion cause the rare autosomal dominant neurodegenerative condition Charcot-Marie-Tooth disease type 2A (CMT2A), for which there is currently no disease-altering therapy. Moreover, accumulating experimental evidence supports an important role for MFN1 and MFN2 in heart disease. A pharmacological means of enhancing mitofusin function has the potential to correct the underlying cause of CMT2A and other cardiac or neurodegenerative diseases caused by mitochondrial dys-dynamism.

MFN1 and MFN2 form homo (MFN1-MFN1 or MFN2-MFN2) or hetero (MFN1-MFN2) trans-dimers between mitochondria. This process is referred to as mitochondrial tethering, and is the requisite first step in mitochondrial fusion essential for metabolic cellular health (Koshiba, T., et al.; *Science* 305:858-62, 2004). Mitochondrial tethering and fusion depend upon a shift in MFN protein conformation, from a more closed resting state to a more open active state. MFN conformation is regulated by intra-molecular peptide-peptide interactions (PPI) between alpha helices in the stalk region of the protein (Franco, A., et al.; *Nature* 540:74-79, 2016). In human (h)MFN2, phosphorylation of serine 378 by mitochondrial PINK1 kinase promotes a tight alpha helix within the interacting peptide, directing critical Val372, Met 376, and His380 amino acid side chains to their interacting partners Leu727, Leu723, and Lys720 respectively (Rocha, A. G., et al.; *Science* 360:336-41, 2018). A strong PPI promotes a folded protein conformation that decreases the probability of trans MFN-MFN dimer formation between mitochondria (e.g., is unfavorable for mitochondrial tethering/fusion). When serine 378 is not phosphorylated the interacting peptide alpha helix partially unwinds, weakening the PPI and increasing the probability that the protein will unfold to permit MFN trans-dimerization and subsequent mitochondrial fusion (Rocha, A. G., et al.; *Science* 2018).

Franco, et al. (Franco, A., et al.; *Nature* 2016) described an 18 amino acid peptide, modified slightly from hMFN2 amino acids 367-384, that competitively inhibited intra-molecular PPI in MFN1 and MFN2, thus promoting the protein conformation favoring mitochondrial fusion. By understanding the critical interacting amino acids within this activator peptide, a pharmacophore model was developed leading to identification of a prototype small molecule mitofusin activator, Chimera B-A/I, which mimicked mitofusin activator peptide effects by promoting mitochondrial fusion after topical application to mitofusin deficient cultured cells and by increasing mitochondrial motility in ex vivo CMT2A nerves (Rocha, A. G., et al.; Science 2018). Clinical application of small molecule mitofusin activators having drug-like properties promises the first disease-altering therapy for CMT2A and may open the door to a novel therapeutic approach of enhancing mitochondrial fusion in multiple diseases with impaired mitochondrial dynamics.

Mitochondria-Associated Diseases, Disorders, or Conditions

The present disclosure provides for compositions and methods of treatment for treating mitochondria-related diseases, disorders, or conditions, including diseases or disorders associated with MFN1 and/or MFN2 and mitochondrial dysfunction. A mitochondria-associated disease, disorder, or condition may be a disease primarily caused by or secondarily associated with mitochondrial dysfunction, fragmentation, or loss-of-fusion, or associated with dysfunction in MFN1 or MFN2 catalytic activity or conformational unfolding. Mitochondrial dysfunction may be caused by genetic mutations of mitofusins or other (nuclear or mitochondrial encoded) genes, or may be caused by physical, chemical, or environmental injury to the CNS or PNS.

Mitochondria transit within cells and undergo fusion to exchange genomes and promote mutual repair. Mitochondrial fusion and subcellular trafficking are mediated in part by MFN1 and MFN2. Genetic mutations in MFN2 that suppress mitochondrial fusion and motility cause Charcot-Marie-Tooth Disease, type 2A (CMT2A), the most common heritable axonal neuropathy. Mitochondrial fragmentation, dysfunction, and dysmotility are also central features of other genetic neurodegenerative syndromes, such as amyotrophic lateral sclerosis, Huntington's disease, Parkinson's disease, and Alzheimer's disease. Because no therapeutics exist that directly enhance mitochondrial fusion or trafficking, these diseases are unrelenting and considered irreversible.

Examples of mitochondria-associated diseases, disorders, and conditions include, but are not limited to, Alzheimer's disease, Parkinson's disease, Huntington's disease, Charcot-Marie-Tooth Disease (type 2A) (CMT), hereditary motor and sensory neuropathy, autism, ADOA, muscular dystrophy, Lou Gehrig's disease, cancer, mitochondrial myopathy, DAD, LHON, Leigh syndrome, subacute sclerosing encephalopathy, NARP, MNGIE, MERRF, MELAS, mtDNA depletion, MNGIE, dysautonomic mitochondrial myopathy, mitochondrial channelopathy, and/or PDCD/PDH.

Symptoms that may be treated with the methods as described herein include, but are not limited to, poor growth, loss of muscle coordination, muscle paralysis and atrophy, visual problems, hearing problems, learning disabilities, heart disease, liver disease, kidney disease, gastrointestinal disorders, respiratory disorders, neurological problems, autonomic dysfunction, and dementia.

Neurodegenerative Disease

As described herein, trans-stereoisomer 6-phenylhexanamide derivative mitofusin activators may rapidly reverse mitochondrial dysmotility in sciatic nerve axons of a mouse model of Charcot-Marie-Tooth disease, type 2A. Because impaired mitochondrial fusion, fitness, and/or trafficking also contribute to neuronal degeneration in various neurodegenerative diseases (e.g., in Charcot-Marie-Tooth disease (CMT2A), Huntington's disease, Parkinson's disease, and Alzheimer's disease, and especially in ALS), the present disclosure provides for compositions (e.g., compositions containing mitofusin activators) and methods to treat such neurodegenerative diseases, disorders, and/or conditions.

Examples of neurodegenerative diseases, disorders and conditions include a disease of impaired neuronal mitochondrial dynamism or trafficking, such as, but not limited to, a hereditary motor and sensory neuropathy (HMSN) (e.g., CMT1 (a dominantly inherited, hypertrophic, predominantly demyelinating form), CMT2 (a dominantly inherited predominantly axonal form), Dejerine-Sottas (severe form with onset in infancy), CMTX (inherited in an X-linked manner), and CMT4 (includes the various demyelinating autosomal recessive forms of Charcot-Marie-Tooth disease); hereditary sensory and autonomic neuropathy type IE, hereditary sensory and autonomic neuropathy type II, hereditary sensory and autonomic neuropathy type V, HMSN types 1A and 1B (e.g., dominantly inherited hypertrophic demyelinating neuropathies), HMSN type 2 (e.g., dominantly inherited neuronal neuropathies), HMSN type 3 (e.g., hypertrophic neuropathy of infancy [Dejerine-Sottas]), HMSN type 4 (e.g., hypertrophic neuropathy [Refsum] associated with phytanic acid excess), HMSN type 5 (associated with spastic paraplegia), and/or HMSN type 6 (e.g., with optic atrophy)).

Other examples of neurodegenerative diseases, disorders, and conditions include, but are not limited to, Alzheimer's disease, ALS, Alexander disease, Alpers' disease, Alpers-Huttenlocher syndrome, alpha-methylacyl-CoA racemase deficiency, Andermann syndrome, Arts syndrome, ataxia neuropathy spectrum, ataxia (e.g., with oculomotor apraxia, autosomal dominant cerebellar ataxia, deafness, and narcolepsy), autosomal recessive spastic ataxia of Charlevoix-Saguenay, Batten disease, beta-propeller protein-associated neurodegeneration, cerebro-oculo-facio-skeletal syndrome (COFS), corticobasal degeneration, CLN1 disease, CLN10 disease, CLN2 disease, CLN3 disease, CLN4 disease, CLN6 disease, CLN7 disease, CLN8 disease, cognitive dysfunction, congenital insensitivity to pain with anhidrosis, dementia, familial encephalopathy with neuroserpin inclusion bodies, familial British dementia, familial Danish dementia, fatty acid hydroxylase-associated neurodegeneration, Friedreich's Ataxia, Gerstmann-Straussler-Scheinker Disease, GM2-gangliosidosis (e.g., AB variant), HMSN type 7 (e.g., with retinitis pigmentosa), Huntington's disease, infantile neuroaxonal dystrophy, infantile-onset ascending hereditary spastic paralysis, infantile-onset spinocerebellar ataxia, juvenile primary lateral sclerosis, Kennedy's disease, Kuru, Leigh's Disease, Marinesco-Sjögren syndrome, mild cognitive impairment (MCI), mitochondrial membrane protein-associated neurodegeneration, motor neuron disease, monomelic amyotrophy, motor neuron diseases (MND), multiple system atrophy, multiple system atrophy with orthostatic hypotension (Shy-Drager Syndrome), multiple sclerosis, multiple system atrophy, neurodegeneration in down's syndrome (NDS), neurodegeneration of aging, neurodegeneration with brain iron accumulation, neuromyelitis optica, pantothenate kinase-associated neurodegeneration, opsoclonus myoclonus, prion disease, progressive multifocal leukoencephalopathy, Parkinson's disease, Parkinson's disease-related disorders, polycystic lipomembranous osteodysplasia with sclerosing leukoencephalopathy, prion disease, progressive external ophthalmoplegia, riboflavin transporter deficiency neuronopathy, Sandhoff disease, spinal muscular atrophy (SMA), spinocerebellar ataxia (SCA), striatonigral degeneration, transmissible spongiform encephalopathies (prion diseases), and/or Wallerian-like degeneration.

Charcot-Marie-Tooth (CMT) Disease Type 2A

Charcot-Marie-Tooth type 2A (CMT2A) disease is an example of a non-curable neurodegenerative disease/axonal neuropathy, disorder, or condition caused by mutations of MFN2 and for which there are currently no disease-modifying treatments. As described herein, it was discovered that severely impaired mitochondrial transport from neuron cell body in the spinal cord to distal neuronal synapse in the lower leg or hand (in addition to smaller mitochondria size as is widely recognized) is a central factor in CMT2A disease onset and progression. CMT2A is a progressive neuromuscular disease that typically causes muscle weakness and wasting in the distal legs/feet in children of ages 1-8 years, then upper limbs, ultimately producing severe muscle wasting, skeletal deformities, and permanent disability. The present disclosure provides for the correction of impaired neuronal mitochondria transport as a therapeutic target in this disease. Data showed that administration of a trans-6-phenylhexanamide mitofusin activators promoted the mitochondria to move along neuronal axons in mouse models where mitochondria were not previously moving, and reversed disease-associated defects in neuromuscular function, which is applicable in any neuropathy (e.g., Huntington's disease, ALS, ALS-like sclerosis, and/or Alzheimer's disease).

Neurological and Neurodegenerative Diseases

As described herein, trans-4-hydroxycyclohexyl 6-phenylhexanamide derivative mitofusin activators may rapidly reverse mitochondrial dysmotility in sciatic nerve axons of a mouse model of Charcot-Marie-Tooth disease type 2A. It is currently believed that impaired mitochondrial trafficking also contribute to neuronal degeneration in various neurological diseases (e.g., in Huntington's disease, Parkinson's disease, and Alzheimer's disease, and especially in ALS). As such, the present disclosure provides for methods and compositions to treat neurological diseases, disorders, or conditions. For example, a neurological disease, disorder, or condition may be, but is not limited to, abulia; agraphia; alcoholism; alexia; alien hand syndrome; Allan-Herndon-Dudley syndrome; alternating hemiplegia of childhood; Alzheimer's disease; amaurosis fugax; amnesia; ALS; aneurysm; angelman syndrome; anosognosia; aphasia; apraxia; arachnoiditis; Arnold-Chiari malformation; asomatognosia; Asperger syndrome; ataxia; attention deficit hyperactivity disorder; atr-16 syndrome; auditory processing disorder; autism spectrum; Behcets disease; bipolar disorder; Bell's palsy; brachial plexus injury; brain damage; brain injury; brain tumor; Brody myopathy; Canavan disease; capgras delusion; carpal tunnel syndrome; causalgia; central pain syndrome; central pontine myelinolysis; centronuclear myopathy; cephalic disorder; cerebral aneurysm; cerebral arteriosclerosis; cerebral atrophy; cerebral autosomal dominant arteriopathy with subcortical infarcts and leukoencephalopathy (CADASIL); cerebral dysgenesis-neuropathy-ichthyosis-keratoderma syndrome (CEDNIK syndrome); cerebral gigantism; cerebral palsy; cerebral vasculitis; cervical spinal stenosis; Charcot-Marie-Tooth disease; chiari malformation; chorea; chronic fatigue syndrome; chronic inflammatory demyelinating polyneuropathy (CIDP); chronic pain; Cockayne syndrome; Coffin-Lowry syndrome; coma; complex regional pain syndrome; compression neuropathy; congenital facial diplegia; corticobasal degeneration; cranial arteritis; craniosynostosis; Creutzfeldt-Jakob disease; cumulative trauma disorders; Cushing's syndrome; cyclothymic disorder; cyclic vomiting syndrome (CVS); cytomegalic inclusion body disease (CIBD); cytomegalovirus infection; Dandy-Walker syndrome; dawson disease; de Morsier's syndrome; Dejerine-Klumpke palsy; Dejerine-Sottas disease; delayed sleep phase syndrome; dementia; dermatomyositis; developmental coordination disorder; diabetic neuropathy; diffuse sclerosis; diplopia; disorders of consciousness; down syndrome; Dravet syndrome; duchenne muscular dystrophy; dysarthria; dysautonomia; dyscalculia; dysgraphia; dyskinesia; dyslexia; dystonia; empty sella syndrome; encephalitis; encephalocele; encephalotrigeminal angiomatosis; encopresis; enuresis; epilepsy; epilepsy-intellectual disability in females; erb's palsy; erythromelalgia; essential tremor; exploding head syndrome; Fabry's disease; Fahr's syndrome; fainting; familial spastic paralysis; febrile seizures; Fisher syndrome; Friedreich's ataxia; fibromyalgia; Foville's syndrome; fetal alcohol syndrome; fragile x syndrome; fragile x-associated tremor/ataxia syndrome (FXTAS); Gaucher's disease; generalized epilepsy with febrile seizures plus; Gerstmann's syndrome; giant cell arteritis; giant cell inclusion disease; globoid cell leukodystrophy; gray matter heterotopia; Guillain-Barré syndrome; generalized anxiety disorder; HTLV-1 associated myelopathy; Hallervorden-Spatz syndrome; head injury; headache; hemifacial spasm; hereditary spastic paraplegia;

heredopathia atactica polyneuritiformis; herpes zoster oticus; herpes zoster; Hirayama syndrome; Hirschsprung's disease; Holmes-Adie syndrome; holoprosencephaly; Huntington's disease; hydranencephaly; hydrocephalus; hypercortisolism; hypoxia; immune-mediated encephalomyelitis; inclusion body myositis; incontinentia pigmenti; infantile refsum disease; infantile spasms; inflammatory myopathy; intracranial cyst; intracranial hypertension; isodicentric 15; Joubert syndrome; Karak syndrome; Kearns-Sayre syndrome; Kinsbourne syndrome; Kleine-Levin syndrome; Klippel Feil syndrome; Krabbe disease; Kufor-Rakeb syndrome; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; leukoencephalopathy with vanishing white matter; lewy body dementia; lissencephaly; locked-in syndrome; Lou Gehrig's disease (amyotrophic lateral sclerosis (ALS)); lumbar disc disease; lumbar spinal stenosis; lyme disease—neurological sequelae; Machado-Joseph disease (spinocerebellar ataxia type 3); macrencephaly; macropsia; mal de debarquement; megalencephalic leukoencephalopathy with subcortical cysts; megalencephaly; Melkersson-Rosenthal syndrome; menieres disease; meningitis; Menkes disease; metachromatic leukodystrophy; microcephaly; micropsia; migraine; Miller Fisher syndrome; mini-stroke (transient ischemic attack); misophonia; mitochondrial myopathy; mobius syndrome; monomelic amyotrophy; Morvan syndrome; motor neurone disease—see ALS; motor skills disorder; moyamoya disease; mucopolysaccharidoses; multi-infarct dementia; multifocal motor neuropathy; multiple sclerosis; multiple system atrophy; muscular dystrophy; myalgic encephalomyelitis; myasthenia gravis; myelinoclastic diffuse sclerosis; myoclonic encephalopathy of infants; myoclonus; myopathy; myotubular myopathy; myotonia congenita; narcolepsy; neuro-Behçet's disease; neurofibromatosis; neuroleptic malignant syndrome; neurological manifestations of aids; neurological sequelae of lupus; neuromyotonia; neuronal ceroid lipofuscinosis; neuronal migration disorders; neuropathy; neurosis; Niemann-Pick disease; non-24-hour sleep-wake disorder; nonverbal learning disorder; O'Sullivan-McLeod syndrome; occipital neuralgia; occult spinal dysraphism sequence; Ohtahara syndrome; olivopontocerebellar atrophy; opsoclonus myoclonus syndrome; optic neuritis; orthostatic hypotension; otosclerosis; overuse syndrome; palinopsia; paresthesia; Parkinson's disease; paramyotonia congenita; paraneoplastic diseases; paroxysmal attacks; Parry-Romberg syndrome; pediatric autoimmune neuropsychiatric disorders associated with streptococcoal infections (PANDAS); Pelizaeus-Merzbacher disease; periodic paralyses; peripheral neuropathy; pervasive developmental disorders; phantom limb/phantom pain; photic sneeze reflex; phytanic acid storage disease; Pick's disease; pinched nerve; pituitary tumors; pmg; polyneuropathy; polio; polymicrogyria; polymyositis; porencephaly; post-polio syndrome; postherpetic neuralgia (phn); postural hypotension; Prader-Willi syndrome; primary lateral sclerosis; prion diseases; progressive hemifacial atrophy; progressive multifocal leukoencephalopathy; progressive supranuclear palsy; prosopagnosia; pseudotumor cerebri; quadrantanopia; quadriplegia; rabies; radiculopathy; Ramsay Hunt syndrome type 1; Ramsay Hunt syndrome type 2; Ramsay Hunt syndrome type 3—see Ramsay-Hunt syndrome; Rasmussen encephalitis; reflex neurovascular dystrophy; refsum disease; REM sleep behavior disorder; repetitive stress injury; restless legs syndrome; retrovirus-associated myelopathy; Rett syndrome; Reye's syndrome; rhythmic movement disorder; Romberg syndrome; Saint Vitus' dance; Sandhoff disease; Schilder's disease (two distinct conditions); schizencephaly; sensory processing disorder; septo-optic dysplasia; shaken baby syndrome; shingles; Shy-Drager syndrome; Sjögren's syndrome; sleep apnea; sleeping sickness; snatiation; Sotos syndrome; spasticity; spina bifida; spinal cord injury; spinal cord tumors; spinal muscular atrophy; spinal and bulbar muscular atrophy; spinocerebellar ataxia; split-brain; Steele-Richardson-Olszewski syndrome; stiff-person syndrome; stroke; Sturge-Weber syndrome; stuttering; subacute sclerosing panencephalitis; subcortical arteriosclerotic encephalopathy; superficial siderosis; Sydenham's chorea; syncope; synesthesia; syringomyelia; tarsal tunnel syndrome; tardive dyskinesia; tardive dysphrenia; Tarlov cyst; Tay-Sachs disease; temporal arteritis; temporal lobe epilepsy; tetanus; tethered spinal cord syndrome; Thomsen disease; thoracic outlet syndrome; tic douloureux; Todd's Paralysis; tourette syndrome; toxic encephalopathy; transient ischemic attack; transmissible spongiform encephalopathies; transverse myelitis; traumatic brain injury; tremor; trichotillomania; trigeminal neuralgia; tropical spastic paraparesis; trypanosomiasis; tuberous sclerosis; 22q13 deletion syndrome; Unverricht-Lundborg disease; vestibular schwannoma (acoustic neuroma); Von Hippel-Lindau disease (VHL); viliuisk encephalomyelitis (VE); Wallenberg's syndrome; west syndrome; whiplash; Williams syndrome; Wilson's disease; y-linked hearing impairment; and/or Zellweger syndrome.

Chemotherapy-Induced Peripheral Neuropathy (CIPN)

Cancer chemotherapy-induced sensory and motor neuropathies may be prevented or treated with the compositions and methods described herein. Although cancer continues to be a leading cause of mortality world-wide, early detection and improved cancer chemotherapeutics preferentially attacking rapidly dividing cells are favorably impacting this disease. Consequently, the number of cancer survivors is increasing and collateral detrimental effects of successful cancer therapy are a growing problem for cancer survivors. Chemotherapy-induced peripheral neuropathy is one of the most common complications of cancer chemotherapy, affecting 20% of all patients and almost 100% of patients receiving high doses of chemotherapeutic agents. Dose-dependent neurotoxicity of motor and sensory neurons can lead to chronic pain, hypersensitivity to hot, cold, and mechanical stimuli, and/or impaired neuromuscular control. The most common chemotherapeutic agents linked to CIPN are platinum, vinca alkaloids, taxanes, epothilones, and the targeted proteasome inhibitor, bortezomib.

CIPN most commonly affects peripheral sensory neurons whose cell bodies are located in dorsal root ganglia lacking the blood-brain barrier that protects other components of the central and peripheral nervous system. Unprotected dorsal root ganglion neurons are more sensitive to neuronal hyperexcitability and innate immune system activation evoked by circulating cytotoxic chemotherapeutic agents. CIPN affects quality of life, and is potentially disabling, because it provokes chronic neuropathic pain that, like other causes of neuralgia (e.g., post herpetic neuralgia, diabetic mononeuropathy), is refractory to analgesic therapy. Motor nerve involvement commonly manifests as loss of fine motor function with deterioration in hand writing, difficulty in buttoning clothes or sewing, and sometimes upper and lower extremity weakness or loss of endurance. CIPN typically manifests within weeks of chemotherapy and in many cases improves after chemotherapy treatment ends, although residual pain, sensory, or motor defects are observed in one third to one half of affected patients. Unfortunately, CIPN-limited chemotherapy dosing can lead to delays, reduction, or interruption of cancer treatment, thus shortening survival.

Mitochondrial dysfunction and oxidative stress are implicated in CIPN because of observed ultrastructural morphological abnormalities, impaired mitochondria DNA transcription and replication, induction of mitochondrial apoptosis pathways, and reduction of experimental CIPN signs by anticipatory mitochondrial protection. As described herein, trans-4-hydroxycyclohexyl 6-phenylhexanamide derivative mitofusin activators may enhance overall mitochondrial function in damaged neurons, increase mitochondrial transport to areas of neuronal damage, and accelerate in vitro neuron repair/regeneration after chemotherapy-induced damage. For this reason, it is believed that trans-4-hydroxycyclohexyl 6-phenylhexanamide derivative mitofusin activators may reduce neuronal injury conferred by chemotherapeutic agents in CIPN and accelerate regeneration/repair of nerves damaged by chemotherapeutic anticancer agents. Further testing of the CIPN damage prevention/repair and regeneration hypothesis will be further developed with the trans-4-hydroxycyclohexyl 6-phenylhexanamide derivative mitofusin activators by evaluating their in vivo effectiveness. As such, the present disclosure provides for compositions and methods to treat cancer chemotherapy induced nerve injury and neuropathy.

CNS or PNS Injury or Trauma

Injury in the CNS or PNS (e.g., trauma to the CNS or PNS, crush injury, SCI, TBI, stroke, optic nerve injury, or related conditions that involve axonal disconnection) may be treated with the compositions and methods as described herein. The CNS includes the brain and the spinal cord and the PNS is composed of cranial, spinal, and autonomic nerves that connect to the CNS.

Damage to the nervous system caused by mechanical, thermal, chemical, or ischemic factors may impair various nervous system functions such as memory, cognition, language, and voluntary movement. Most often, this is through accidental crush or transection of nerve tracts, or as an unintended consequence of medical interventions, that interrupt normal communications between nerve cell bodies and their targets. Other types of injuries may include disruption of the interrelations between neurons and their supporting cells or the destruction of the blood-brain barrier.

As described herein, trans-4-hydroxycyclohexyl 6-phenylhexanamide derivative mitofusin activators may rapidly reverse mitochondrial dysmotility in neurons from mice or patients with various genetic or chemotherapeutic neurodegenerative diseases, in axons injured by chemotherapeutic agents, and in axons severed by physical injury. For this reason, it is believed that enhancing mitochondrial trafficking with trans-4-hydroxycyclohexyl 6-phenylhexanamide derivative mitofusin activators may enhance regeneration/repair of physically damaged nerves, as in vehicular and sports injuries, penetration trauma from military or criminal actions, and iatrogenic injury during invasive medical procedures. Further testing of the injury-regeneration hypothesis will be further developed with the small molecule mitofusin activators for evaluation of their in vivo effectiveness. As such, the present disclosure provides for compositions and methods to treat physical nerve injury.

As disclosed herein, mitochondrial motility is implicated in neuropathy. It is believed that mitochondrial motility is also implicated in traumatic crush or severance nerve injuries. After nerve laceration or crush injury, nerves will either regenerate and restore neuromuscular function or fail to regenerate such that neuromuscular function in permanently impaired. Trans-4-hydroxycyclohexyl 6-phenylhexanamide derivative mitofusin activators, as described herein, may increase mitochondrial trafficking, enabling the nerve to regenerate after traumatic injuries.

Formulation

The agents and compositions described herein may be formulated by any conventional manner using one or more pharmaceutically acceptable carriers or excipients as described previously (e.g., Remington's Pharmaceutical Sciences (A. R. Gennaro, Ed.), 21st edition, ISBN: 0781746736 (2005), which is incorporated herein by reference with respect to its disclosure of pharmaceutically acceptable carriers). Such formulations will contain a therapeutically effective amount of a biologically active agent described herein, which may be in purified form, together with a suitable amount of carrier to provide the form for proper administration to a subject.

The term "formulation" refers to a preparation of a drug in a form suitable for administration to a subject such as a human or animal pet or livestock. Thus, a "formulation" may include pharmaceutically acceptable excipients, including diluents or carriers.

The term "pharmaceutically acceptable," as used herein, describes substances or components that do not cause unacceptable losses of pharmacological activity or unacceptable adverse side effects. One of skill in the art will be familiar with suitable pharmaceutically acceptable substances. Examples of pharmaceutically acceptable ingredients include those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF may also be used.

The term "pharmaceutically acceptable excipient," as used herein, includes solvents, dispersion media, coatings, antibacterial agents, antifungal agents, isotonic, and absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients may also be incorporated into the compositions.

A "stable" formulation or composition refers to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

A formulation should suit the desired mode of administration. The agents of use with the current disclosure may be formulated by known methods for administration to a subject using several routes including, but not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations may also be used to affect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period. In order to maintain a near-constant level of an agent in the body, the agent may be released from the dosage form at a rate that will replace the amount of agent being metabolized or excreted from the body. The controlled-release of an agent may be stimulated by various inducers (e.g., change in pH, change in temperature, enzymes, water, or other physiological conditions or molecules).

Agents or compositions described herein may also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided herein is a process of treating a mitochondria-associated disease, disorder, or condition in a subject in need of administration of a therapeutically effective amount of a trans-4-hydroxycyclohexyl 6-phenylhexanamide derivative mitofusin activator to prevent or treat a mitochondria-associated disease, disorder, or condition.

For example, the compositions and methods described herein may be used as a primary therapy for Charcot-Marie-Tooth or as an adjunctive therapy for Huntington's disease, Parkinson's disease, Alzheimer's disease, or ALS to retard or reverse disease progression.

As another example, the compositions and methods described herein may be used for the prevention or treatment of chemotherapy-induced peripheral neuropathy. For example as pre- and post-therapy for individuals undergoing scheduled chemotherapy for the treatment of cancer. Pre- and post-chemotherapy treatment with trans-4-hydroxycyclohexyl 6-phenylhexanamide derivative mitofusin activators may prevent, attenuate, and accelerate recovery from chemotherapy-induced peripheral neuropathy. This therapy may minimize sensory and motor neuron susceptibility to chemotherapeutic agents and accelerate repair of chemotherapy-induced neuronal damage by promoting mitochondrial fitness and localization to areas of injury and regrowth.

As yet another example, the compositions and methods described herein may be used for the treatment of a physical injury. For example, as a primary therapy for any contusive or laceration injury involving the spine or peripheral nerves (perhaps even the brain, (i.e., concussion), such as motor vehicle or sports injuries. This therapy may help restore normal motor function by augmenting regeneration and repair of injured neurons.

Methods described herein are generally performed on a subject in need thereof. A subject in need of the therapeutic methods described herein may be a subject having, diagnosed with, suspected of having, or at risk for developing a mitochondria-associated disease, disorder, or condition. A determination of the need for treatment will typically be assessed by a history and physical exam consistent with the disease or condition at issue. Diagnosis of the various conditions treatable by the methods described herein is within the skill of the art. The subject may be an animal subject, including a mammal, such as horses, cows, dogs, cats, sheep, pigs, mice, rats, monkeys, hamsters, guinea pigs, chickens, and humans. For example, the subject may be a human subject.

Generally, a safe and effective amount of a trans-4-hydroxycyclohexyl 6-phenylhexanamide derivative mitofusin activator is, for example, that amount that would cause the desired therapeutic effect in a subject while minimizing undesired side effects. In various aspects, an effective amount of a mitofusin activator described herein may substantially inhibit mitochondria-associated disease, disorder, or condition, slow the progress of mitochondria-associated disease, disorder, or condition, or limit the development of mitochondria-associated disease, disorder, or condition. For example, a desired therapeutic effect may be a delay in peripheral neuropathy (e.g., over the course of three years) compared to placebo assessed by slower increase in modified composite CMT neuropathy score. As another example, a desired therapeutic effect may be reversal or absence of progression of peripheral neuropathy compared to placebo, as indicated by lower or stable modified composite CMT neuropathy score. As yet another example, a desired therapeutic effect may be reversal or absence of progression of dysregulated motor function or increased regeneration and repair of injured neurons.

According to the methods described herein, administration may be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a mitofusin activator may be employed in pure form or, where such forms exist, in pharmaceutically acceptable salt form and with or without a pharmaceutically acceptable excipient. For example, the compounds of the present disclosure may be administered, at a reasonable benefit/risk ratio applicable to any medical treatment, in a sufficient amount to treat, reverse, prevent, or slow the progression of mitochondria-associated disease, disorder, or condition.

The amount of a composition described herein that may be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein may be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that may be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble, et al.; (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Shamel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, may benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating may also include inhibiting the state, disease, disorder, or condition (e.g., arresting or reducing the development of the disease or at least one clinical or subclinical symptom thereof). Furthermore, treating may include relieving the disease (e.g., causing regression of the state, disease, disorder, or condition or at least one of its clinical or subclinical symptoms). A benefit to a subject to be treated may be either statistically significant or at least perceptible to the subject or to a physician.

Administration of a trans-4-hydroxycyclohexyl 6-phenylhexanamide derivative mitofusin activator may occur as a single event or over a time course of treatment. For example, a mitofusin activator may be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For chronic conditions, treatment could extend from several weeks to several months or even years.

Treatment in accord with the methods described herein may be performed prior to, concurrent with, or after conventional treatment modalities for treating, preventing, or slowing the progression of mitochondria-associated disease, disorder, or condition.

A trans-4-hydroxycyclohexyl 6-phenylhexanamide derivative mitofusin activator may be administered simultaneously or sequentially with another agent, such as an antibiotic, an anti-inflammatory, or another neuroregenerative or neurotherapeutic agent. For example, a trans-4-hydroxycyclohexyl 6-phenylhexanamide derivative mitofusin activator may be administered simultaneously with another agent, such as an antibiotic or an anti-inflammatory. Simultaneous administration may occur through administration of separate compositions, each containing one or more of a mitofusin activator, an antibiotic, an anti-inflammatory, or another agent. Simultaneous administration may occur through administration of one composition containing two or more of a mitofusin activator, an antibiotic, an anti-inflammatory, or another agent. A trans-4-hydroxycyclohexyl 6-phenylhexanamide derivative mitofusin activator may be administered sequentially with an antibiotic, an anti-inflammatory, or another agent. For example, a trans-4-hydroxycyclohexyl 6-phenylhexanamide derivative mitofusin activator may be administered before or after administration of an antibiotic, an anti-inflammatory, or another agent.

Administration

Agents and compositions described herein may be administered according to methods described herein in a variety of means known to the art. The agents and composition may be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration may be parenteral, pulmonary, oral, topical, transdermal (e.g., a transdermal patch) intradermal, intramuscular, intraperitoneal, intravenous, subcutaneous, intranasal, epidural, ophthalmic, buccal, or rectal administration.

Agents and compositions described herein may be administered in a variety of methods well known in the arts. Administration methods may include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump that may be used to administer the agent or composition in a manner similar to that used for delivering insulin or chemotherapy to specific organs or tumors. Typically, using such a system, an agent or composition may be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system may be placed in proximity of a therapeutic target, thus requiring only a fraction of a systemic dosage.

Agents may be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided herein are kits. Such kits may include an agent or composition described herein and, in certain aspects, instructions for administration. Such kits may facilitate performance of the methods described herein. When supplied as a kit, the different components of the composition may be packaged in separate containers and admixed immediately before use. Components include, but are not limited to MFN1, MFN2, activator target peptides, or trans-4-hydroxycyclohexyl 6-phenylhexanamide derivative mitofusin activators. Such packaging of the components separately can, if desired, be presented in a pack or dispenser device, which may contain one or more unit dosage forms containing the composition. The pack may, for example, comprise metal or plastic foil such as a blister pack. Such packaging of the components separately may also, in certain instances, permit long-term storage without losing activity of the components.

Kits may also include reagents in separate containers (e.g., sterile water or saline) to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that may be pierced by a hypodermic injection needle. Other containers may have two compartments that are separated by a readily removable membrane that upon removal permits the components to mix. Removable membranes may be glass, plastic, rubber, and the like.

In certain aspects, kits may be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols may be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel, et al.; (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Metabolites

Metabolites of trans-(4-hydroxycyclohexyl)-6-phenylhexanamide were isolated following in vivo administration and certain examples were found to be highly active mitofusin activators. Among mitofusin activators that are metabolites of trans-(4-hydroxycyclohexyl)-6-phenylhexanamide include the following compounds:

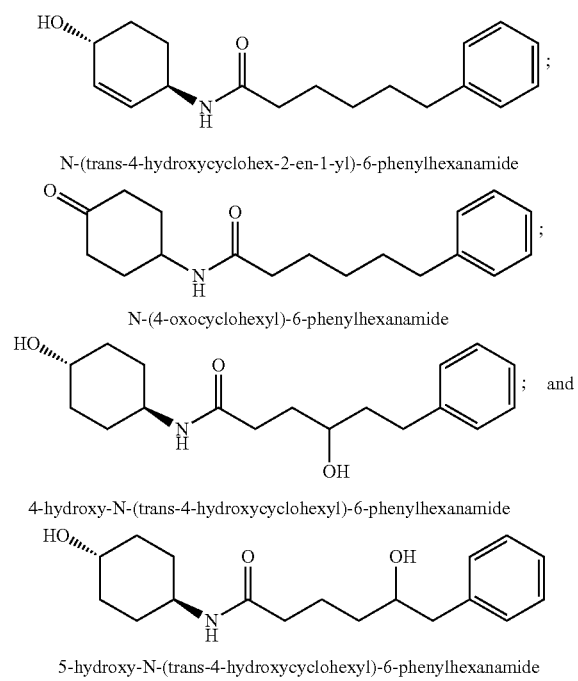

Mitofusin activators having structures analogues to those produced metabolically are also encompassed within the compounds disclosed herein. Any of the foregoing mitofusin activator metabolites may be administered to a subject directly for purposes of managing a mitochondria-associated disease, disorder or condition.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some aspects, numbers expressing quantities of ingredients, properties such as molecular weight, reaction conditions, and so forth, used to describe and claim certain aspects of the present disclosure are to be understood as being modified in some instances by the term "about." In some features, the term "about" is used to indicate that a value includes the standard deviation of the mean for the device or method being employed to determine the value. In some features, the numerical parameters set forth in the written description and attached claims are approximations that may vary depending upon the desired properties sought to be obtained by a particular feature. In some aspects, the numerical parameters should be construed in light of the number of reported significant digits and by applying ordinary rounding techniques. Notwithstanding that the numerical ranges and parameters setting forth the broad scope of some aspects of the present disclosure are approximations, the numerical values set forth in the specific examples are reported as precisely as practicable. The numerical values presented in some aspects of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some aspects, the terms "a" and "an" and "the" and similar references used in the context of describing a particular aspect (especially in the context of certain of the following claims) may be construed to cover both the singular and the plural, unless specifically noted otherwise. In some aspects, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are open-ended. For example, any method that "comprises," "has" or "includes" one or more steps is not limited to possessing only those one or more steps and may cover other unlisted steps. Similarly, any composition or device that "comprises," "has" or "includes" one or more features is not limited to possessing only those one or more features and may cover other unlisted features.

All methods described herein may be performed in any suitable order unless otherwise indicated herein or otherwise clearly contradicted by context. The use of any and all examples, or exemplary language (e.g., "such as") provided with respect to certain aspects herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements, embodiments, aspects, or features of the present disclosure disclosed herein are not to be construed as limitations. Each group member may be referred to and claimed individually or in any combination with other members of the group or other elements found herein. One or more members of a group may be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments, features, or aspects are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus may be considered to constitute examples of modes for its practice. However, those of skill in the art should, in light of the present disclosure, appreciate that many changes may be made in the specific features that are disclosed and still obtain a like or similar result without departing from the spirit and scope of the present disclosure.

Example 1.
N-(cis-4-Hydroxycyclohexyl)-6-phenylhexanamide (MiM 111 cis, Compound 15A)

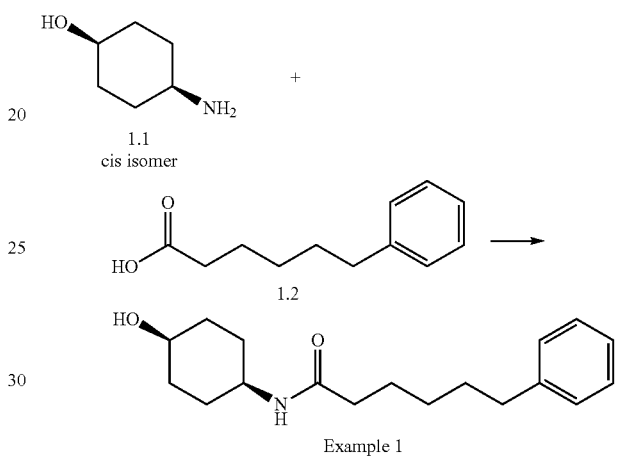

Example 1

To a solution of 6-phenylhexanoic acid 1.2 (200 mg, 1.04 mmol, 196 µL, 1.00 eq.) and cis-4-hydroxycyclohexylamine 1.1 (174 mg, 1.14 mmol, 1.10 eq.) and DIEA (269 mg, 2.08 mmol, 362 µL, 2.00 eq.) in DMF (3 mL) was added HOBt (169 mg, 1.25 mmol, 1.20 eq.) and EDCl (299 mg, 1.56 mmol, 1.50 eq.). The mixture was stirred at 10° C. for 10 hours. The mixture was diluted with water (20 mL) and extracted with EtOAc (10 mL×3). The organic phase was washed with 1M aqueous HCl (30 mL), dried over $Na_2SO_4$, filtered and concentrated under reduced pressure to give a residue. The residue was purified by preparative HPLC. The title compound was obtained as a light yellow gum. MS: m/z=290.1 (M+H)$^+$; $^1$H NMR (400 MHz): MeOD δ 7.25-7.22 (m, 2H), 7.17-7.11 (m, 3H), 3.84 (s, 1H), 3.70-3.65 (m, 1H), 2.60 (t, J=7.6 Hz, 2H), 2.16 (t, J=7.2 Hz, 2H), 1.73-1.65 (m, 3H), 1.65-1.59 (m, 9H), 1.36-1.34 (m, 2H). $^{13}$C NMR (400 MHz): MeOD δ: 175.628, 143.895, 129.579, 129.414, 126.809, 66.945, 37.182, 36.885, 32.558, 32.179, 29.863, 28.074, 27.168.

Example 2.
N-(trans-4-Hydroxycyclohexyl)-6-phenylhexanamide (MiM 111 trans, Compound 15B)

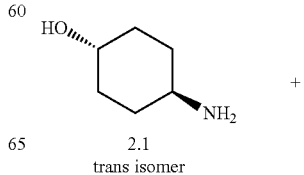

2.1
trans isomer

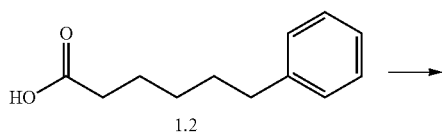

1.2

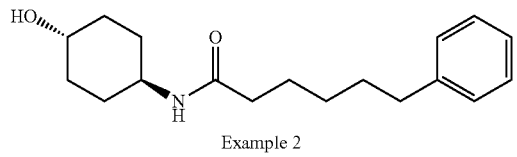

Example 2

To a solution of 6-phenylhexanoic acid 1.2 (200 mg, 1.04 mmol, 196 μL, 1.00 eq.) and trans-4-hydroxycyclohexylamine 2.1 (174 mg, 1.14 mmol, 1.10 eq.) and DIEA (269 mg, 2.08 mmol, 362 μL, 2.00 eq.) in DMF (3 mL) was added HOBt (169 mg, 1.25 mmol, 1.20 eq.) and EDCl (299 mg, 1.56 mmol, 1.50 eq.). The mixture was stirred at 10° C. for 10 hours. The mixture was diluted with water (20 mL) and extracted with EtOAc (10 mL×3). The organic phase was washed with 1M aqueous HCl (30 mL), dried over $Na_2SO_4$, filtered and concentrated under reduced pressure to give a residue. The residue was purified by preparative HPLC. The title compound was obtained as a white solid. MS: m/z=290.1 $(M+H)^+$; $^1$H NMR (400 MHz): MeOD δ 7.25-7.21 (m, 2H), 7.16-7.11 (m, 3H), 3.59-3.48 (m, 1H), 2.60 (t, J=7.6 Hz, 2H), 2.13 (t, J=7.6 Hz, 2H), 2.11-1.92 (m, 2H), 1.92-1.83 (m, 2H), 1.65-1.60 (m, 4H), 1.34-1.19 (m, 6H). $^{13}$C NMR (400 MHz): MeOD δ: 175.660, 143.882, 129.590, 129.441, 126.819, 70.591, 37.231, 36.864, 34.965, 32.519, 31.655, 29.804, 27.098.

Figure 3A:
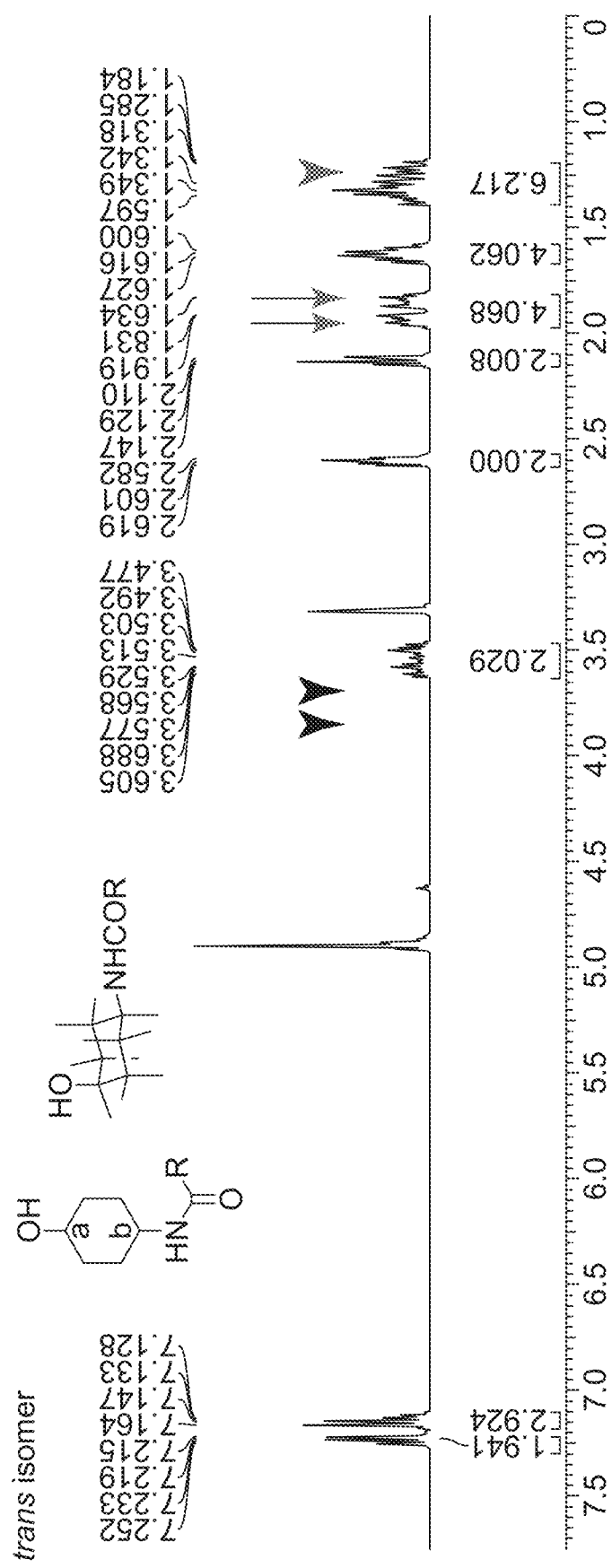
FIGS. 3A-3B depict chemical structures and corresponding NMR spectra of MiM 111 cis- (FIG. 3A) and trans- (FIG. 3B) isostereomers (see e.g., Example 3). Black arrows and arrowhead are specific to cis-isomer; grey arrowheads signify trans-isomer.
Figure 3B:
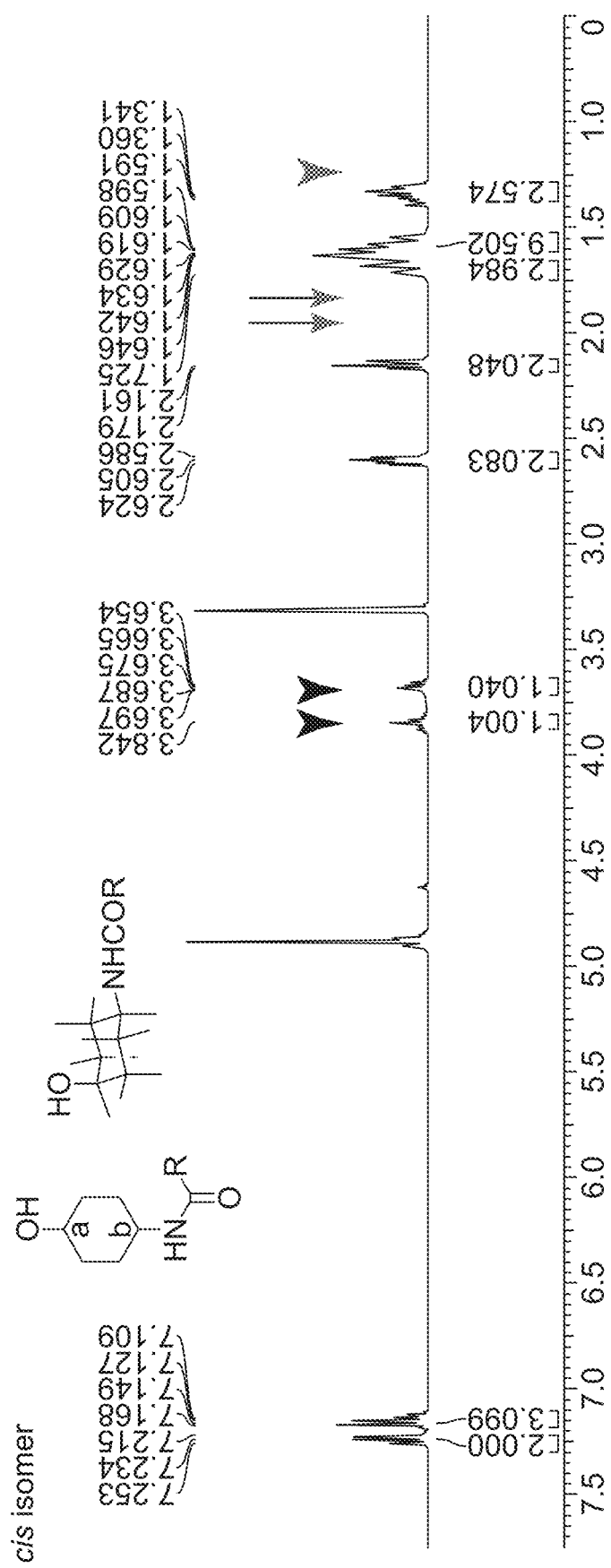

Example 3: The Trans-Stereoisomer of MiM 111 is an Allosteric Mitofusin Agonist, Whereas the Cis-Stereoisomer of MiM 111 is Inactive Previously, chemical syntheses of candidate mitofusin activators sourced starting materials as a mixture of stereoisomers, resulting in products that were also mixtures of 2 or more isomers. It is recognized that target recognition and biological activity can differ between stereoisomers (Sundén, H., et al.; *ChemMedChem* 8:1283-94, 2013; Jafurulla, M., et al.; *Biochim Biophys Acta* 1838:158-63, 2014). However, due to the novelty of small molecule mitofusin activators as a drug class, there are no data describing, nor even computer models that can predict: 1. if stereoisomers affect mitofusin activator efficacy; and 2. if they do, which stereoisomer(s) have superior properties. Accordingly, cis- and trans-diastereomers of N-(4-hydroxycyclohexyl)-6-phenylhexanamide, designated cis- and trans-MiM 111, were individually synthesized, validated, and characterized (FIGS. 3A-3B). Remarkably, the cis form exhibited no detectable mitofusin activating activity, measured as mitochondrial elongation, in either MFN1 or MFN2 deficient murine embryonic fibroblasts (FIGS. 2A-2B). By contrast, the trans form of MiM 111 was equipotent to a prototype mitofusin agonist of the chemical class described in Rocha, et al.; Science 2018, Chimera C. Functional activity of cis- and trans-N-(4-hydroxycyclohexyl)-6-phenylhexanamide mirrored their ability to provoke the characteristic change in MFN2 conformation that underlies its activation (FIG. 2C), mechanistically linking biological effect and target engagement as a function of isomeric structure. The cis- and trans-stereoisomers of MiM 111 had similar in vitro pharmacokinetic profiles (Table 1).

TABLE 1

In vitro functional and pharmacokinetic properties of MiM 111 cis- and trans- diastereomers (Compounds 15A and 15B)

| Cpd | Structure | $EC_{50}$ (nM) Mfn1 KO | $EC_{50}$ (nM) Mfn2 KO | hPPB (%) | mPPB (%) | $t_{1/2}$ HLM (min) | $t_{1/2}$ MLM (min) | PAMPA Pe (nm/sec) |
|---|---|---|---|---|---|---|---|---|
| 15A | 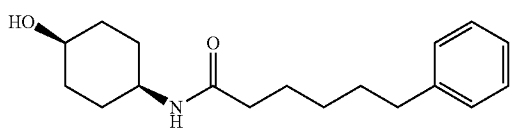 [SMILES: O=C(CCCCCc1ccccc1)N[C@H]1CC[C@@H](O)CC1] | inactive | inactive | 93.9 | 93.8 | 102 | 70 | 42.6 |
| 15B | 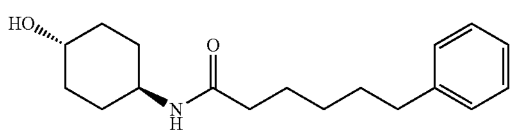 [SMILES: O=C(CCCCCc1ccccc1)N[C@H]1CC[C@H](O)CC1] | 7.7 | 9.5 | 90.4 | 96.7 | >145 | 127 | 22.9 |

Example 4: Trans-Stereoisomers of MiM 111 Having Oxy-Substituted Linkers are Potent Mitofusin Activators with a Spectrum of Passive Membrane Permeability Characteristics The complete series of oxy-substituted linker analogs for trans-N-(4-hydroxycyclohexyl)-6-phenylhexanamide were synthesized and evaluated for fusogenic activity and pharmacokinetic properties. All of the oxy-substituted trans-analogs retained excellent fusogenic activity, but the position of the oxygen within the linker altered the passive membrane permeability characteristics of these compounds, with the carbamate exhibiting 10-fold greater PAMPA, but reduced microsomal stability, compared to parent trans-N-(4-hydroxycyclohexyl)-6-phenylhexanamide (Table 2).

TABLE 2

Functional and pharmacokinetic properties of oxy-substituted linker analogs of trans-MiM 111 ((Compound 15B)

| Cpd | Structure | $EC_{50}$ (nM) | hPPB (%) | mPPB (%) | $t_{1/2}$ HLM (min) | $t_{1/2}$ MLM (min) | PAMPA Pe (nm/sec) |
|---|---|---|---|---|---|---|---|
| 15B | 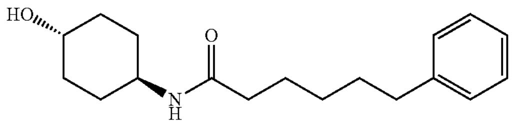 [SMILES: O=C(CCCCCc1ccccc1)N[C@H]1CC[C@H](O)CC1] | 5.54 | 90.4 | 96.7 | >145 | 127 | 22.9 |
| 21 | 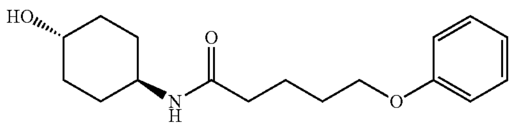 [SMILES: O=C(CCCCOc1ccccc1)N[C@H]1CC[C@H](O)CC1] | 9.63 | 80.2 | 81.8 | >145 | >145 | 3.66 |
| 22 | 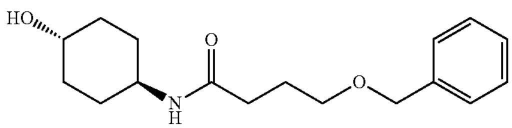 [SMILES: O=C(CCCOCc1ccccc1)N[C@H]1CC[C@H](O)CC1] | 12.92 | 57.1 | 60.4 | >145 | >145 | 1.176 |
| 23 | 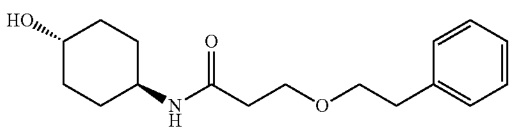 [SMILES: O=C(CCOCCc1ccccc1)N[C@H]1CC[C@H](O)CC1] | 3.31 | 38.2 | 48.5 | >145 | >145 | 2.228 |
| 24 | 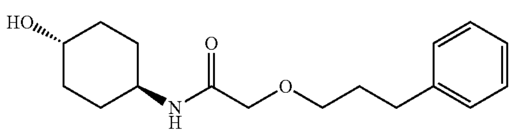 [SMILES: O=C(COCCCc1ccccc1)N[C@H]1CC[C@H](O)CC1] | 7.31 | 55.2 | 66.4 | >145 | >145 | 23.799 |
| 25 | 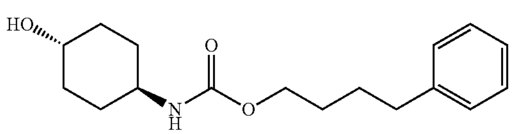 [SMILES: O=C(N[C@H]1CC[C@H](O)CC1)OCCCCc1ccccc1] | 6.28 | 93.3 | 94.8 | 131.3 | 48.9 | 210.149 |

Compounds 21-25 were synthesized similarly to Compound 15B (Example 2), except incorporating an appropriate oxygenated 6-phenylhexanoic acid derivative for 6-phenylhexanoic acid 1.2. Namely, Compounds 21-25 were synthesized by replacing 6-phenylhexanoic acid 1.2 with 5-phenoxypentanoic acid, 4-(benzyloxy)butanoic acid, 3-phenethoxypropanoic acid, 2-(3-phenylpropoxy)acetic acid, or 4-phenylbutylcaronochloridate, respectively.

Compound 21:
HPLC: RT: 2.17 min, purity: 99.9%. LC-MS: RT=0.830 min, m/z=292.3 (M+H)$^+$. $^1$H NMR: 400 MHz, MeOD. δ 7.25 (t, J=8.0 16.4 Hz, 2H), 6.9 (d, J=8.4 Hz, 3H), 3.9 (m, 2H), 3.51-3.63 (m, 2H), 2.24 (s, 2H), 1.92-1.97 (m, 4H), 1.77-1.70 (m, 4H), 1.30-1.37 (m, 4H). $^{13}$C NMR: (400 MHz, MeOD) δ (176, 161, 131, 122, 116, 71.2, 69.2, 37.6, 35.6, 32.3, 30.7, 24.5) ppm.

Compound 22:
HPLC: RT: 1.80 min, purity: 99.8%. LC-MS: RT=0.802 min, m/z=292.3 (2M+Na)$^+$. $^1$H NMR: (400 MHz, MeOD) δ 7.25-7.33 (m, 5H), 4.48 (s, 2H), 3.46-3.59 (m, 4H), 2.24 (t, J=7.2, 2H), 1.82-1.92 (m, 6H), 1.20-1.33 (m, 4H). $^{13}$C NMR: (400 MHz, MeOD) δ (175, 139, 130, 129, 128, 74.0, 70.6, 70.5, 34.9, 34.1, 31.6, 27.2) ppm.

Compound 23:
HPLC: RT: 1.86 min, purity: 97.6%. LC-MS: RT=0.789 min, m/z=292.4 (M+H)$^+$. $^1$H NMR: (400 MHz, MeOD) δ 7.17-7.27 (m, 5H), 3.66-3.70 (m, 4H), 3.49-3.64 (m, 2H), 2.84 (t, J=6.8, 2H), 2.37 (t, J=6.0, 2H), 1.82-1.94 (m, 4H), 1.17-1.34 (m, 4H). $^{13}$C NMR: (400 MHz, MeOD) δ (173, 140, 130, 129, 127, 73.0, 70.5, 68.1, 37.9, 37.2, 34.9, 31.5) ppm.

Compound 24:
HPLC: RT: 2.24 min, purity: 98.3%. LC-MS: RT=0.825 min, m/z=292.1 (M+H)$^+$. $^1$H NMR: (400 MHz, MeOD) δ 7.24-7.28 (m, 2H), 7.15-7.20 (m, 3H), 3.88 (s, 2H), 3.68-3.70 (m, 1H), 3.53-3.56 (m, 1H), 3.50 (t, J=6.4 Hz, 2H), 2.70 (t, J=7.6 Hz, 2H), 1.91-1.96 (m, 4H), 1.86-1.87 (m, 2H), 1.33-1.38 (m, 4H). $^{13}$C NMR: (400 MHz, MeOD) δ (172, 143, 130, 129, 127, 72.1, 71.1, 70.4, 34.9, 33.3, 32.3, 31.4) ppm.

Compound 25:
HPLC: RT: 2.54 min, purity: 99.7%. LC-MS: RT=0.886 min, m/z=292.2 (M+H)$^+$. $^1$H NMR: (400 MHz, MeOD) δ 7.12-7.26 (m, 5H), 4.02 (t, J=6.0, 2H), 3.47-3.52 (m, 1H), 3.33-3.35 (m, 1H), 2.63 (t, J=7.2, 2H), 1.88-1.94 (m, 4H), 1.64-1.66 (m, 4H), 1.1.23-1.31 (m, 4H). $^{13}$C NMR: (400 MHz, MeOD) δ (158, 143, 130, 129, 126, 70.5, 65.6, 50.7, 36.5, 34.9, 31.9, 29.9, 29.1) ppm.

Example 4B: The Cyclic Cyclopropane Backbone Analogue of Trans-Stereoisomer MiM 111 is also Active Compound 26 was synthesized similarly to Compound 15B (Example 2), except incorporating 2-(3-phenylpropyl) cyclopropane-1-carboxylic acid for 6-phenylhexanoic acid 1.2. This compound had an EC$_{50}$ of 5.1 nm, H and M plasma protein binding of 94.4% and 95.5%, H and M liver microsome stability T$^{1/2}$ values of >145 minutes and 114.1 minutes, and a PAMPA assay value of 58.451 nm/s.

Example 5: In Vivo Pharmacological Profiling Shows that Trans-MiM 111 (Compound 15B) is a Clinical Candidate for CMT2A Trans-MiM 111 exhibited high microsomal stability and passive permeability (PAMPA Pe), with a low efflux ratio in NIH MDR1 cells that did not change in the presence of the P-gp inhibitor GF120918 (Table 3), indicating that it is not a P-gp substrate. In this context it was anticipated that microsomal stability would correlate with in vivo plasma t$^{1/2}$, and passive permeability with CNS levels.

TABLE 3

P-gp studies of trans-MiM 111 (Compound 15B)

| Compound ID | GF120918 (+/−) | Mean P$_{app}$ (10$^{-6}$ cm/s) A to B | Mean P$_{app}$ (10$^{-6}$ cm/s) B to A | Efflux Ratio | Mean Recovery % A to B | Mean Recovery % B to A | Note |
|---|---|---|---|---|---|---|---|
| Nadolol | − | 0.26 | ND | ND | 97.88 | ND | Low permeability marker |
| Metoprolol | − | 21.24 | ND | ND | 105.27 | ND | High permeability marker |
| Digoxin | − | 0.11 | 13.36 | 123.06 | 98.93 | 103.29 | P-gp substrate |
|  | + | 0.73 | 2.05 | 2.81 | 97.04 | 99.34 |  |
| 15B | − | 20.36 | 35.45 | 1.74 | 84.58 | 100.21 | — |
|  | + | 31.88 | 23.21 | 0.73 | 84.76 | 100.61 |  |

This notion was examined by in vivo PK studies in mice, the only species in which pre-clinical models of human CMT2A have been published (Cartoni, R., et al.; *Brain* 133:1460-9, 2010; Bannerman, P., et al.; *PLoS ONE* 11:e0167573, 2016; Zhou, Y., et al.; *J Clin Invest* 130:1756-1771, 2019). A target therapeutic brain level of 10 times the in vitro EC$_{50}$ for each compound, or 30 ng/g (~100 nM), was established.

Figure 4A:
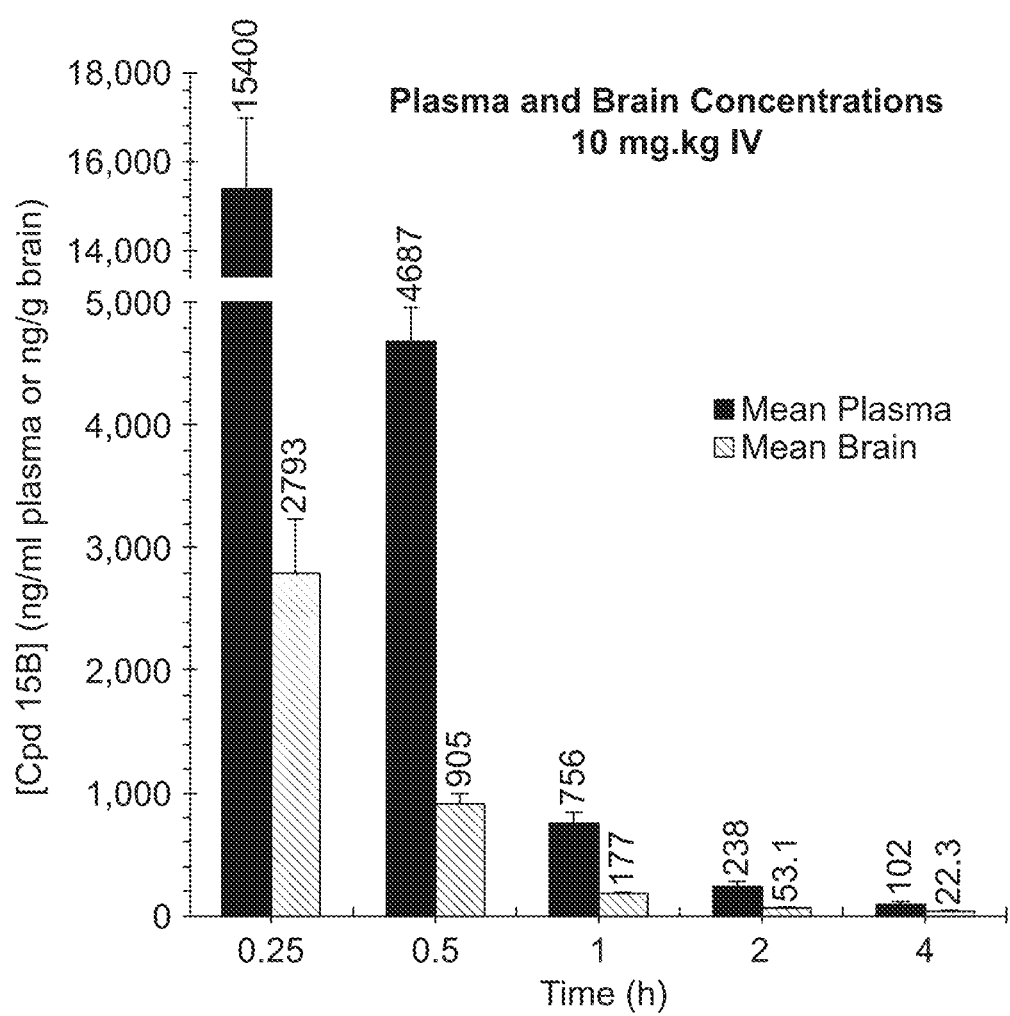
FIGS. 4A-4B depict in vivo (mouse) pharmacokinetic properties of trans-MiM 111 (Cpd 15B) (see e.g., Example 5).

Comparative mouse plasma and brain levels were determined at increasing times after a single 10 mg/kg intravenous (IV) dose. The Vdss (volume of distribution at steady state) of trans-MiM 111 was 0.35 L/kg and peak brain levels were 2,793 ng/g; therapeutic levels (of >30 ng/g) were maintained for more than 2 hours after the single IV dose (FIG. 4A).

Figure 4B:
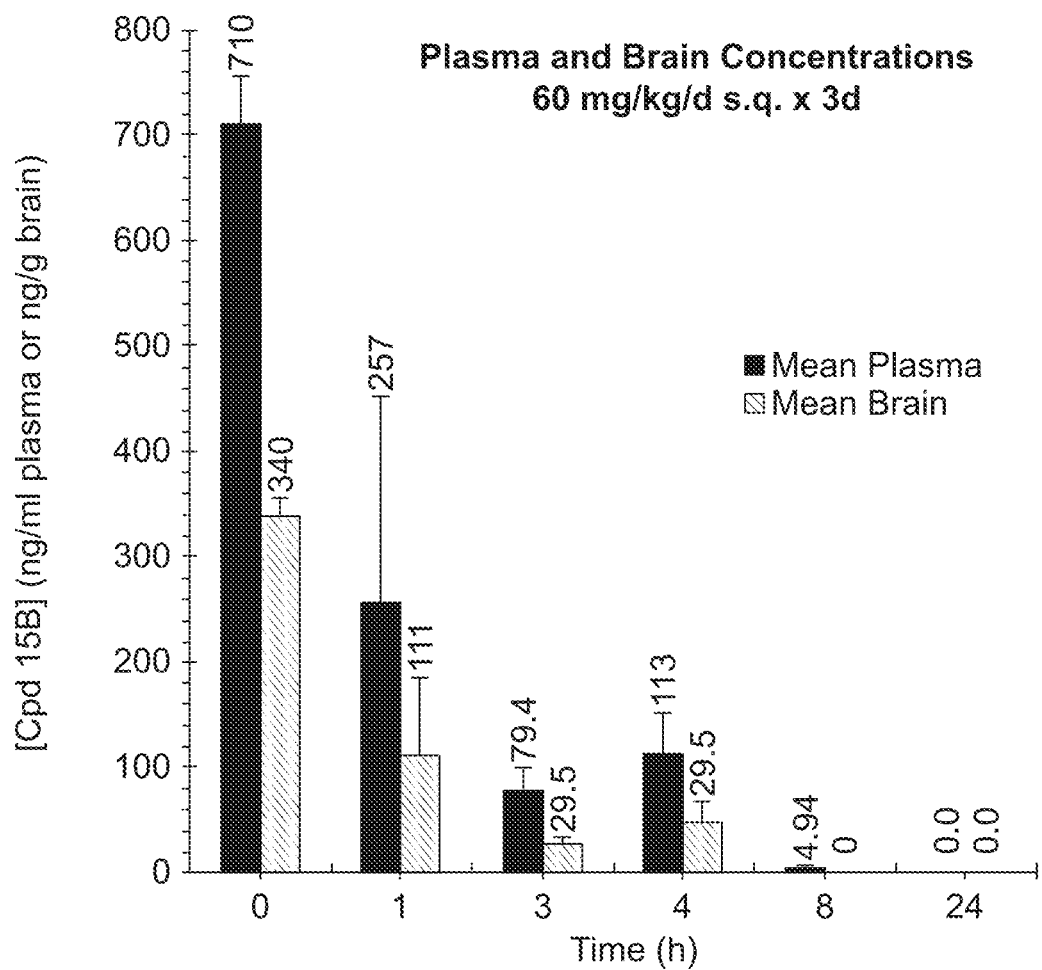

Because of its low Vdss, high Pe, and low efflux in NIH MDR1 cells it was surmised that trans-MiM 111 might accumulate in brains over time. If this were so, then brain levels after single dose administration could be misleading vis-à-vis therapeutic efficacy. To test this idea osmotic mini-pumps were used to deliver trans-MiM 111 subcutaneously (SQ) at a daily dose of 60 mg/kg/day for three days to achieve steady state, and its elimination kinetics were defined after mini-pump removal (FIG. 4B). Trans-MiM 111 plasma half-lives were similar after bolus IV and chronic SQ administration (1.1 hours and 1.33 hours, respectively), but its brain half-life was substantially longer after chronic infusion (3.37 hours vs 1.06 hours after IV). Because it is 96.7% plasma protein bound in mice, the unbound fraction (fu) of trans-MiM 111 is 0.033. Using this factor to convert plasma [Cpd 15B]$_{total}$ to plasma [Cpd 15B]$_{free/unbound}$, the calculated ratio of brain to free plasma level is 10.8 after chronic infusion.

Figure 5A:
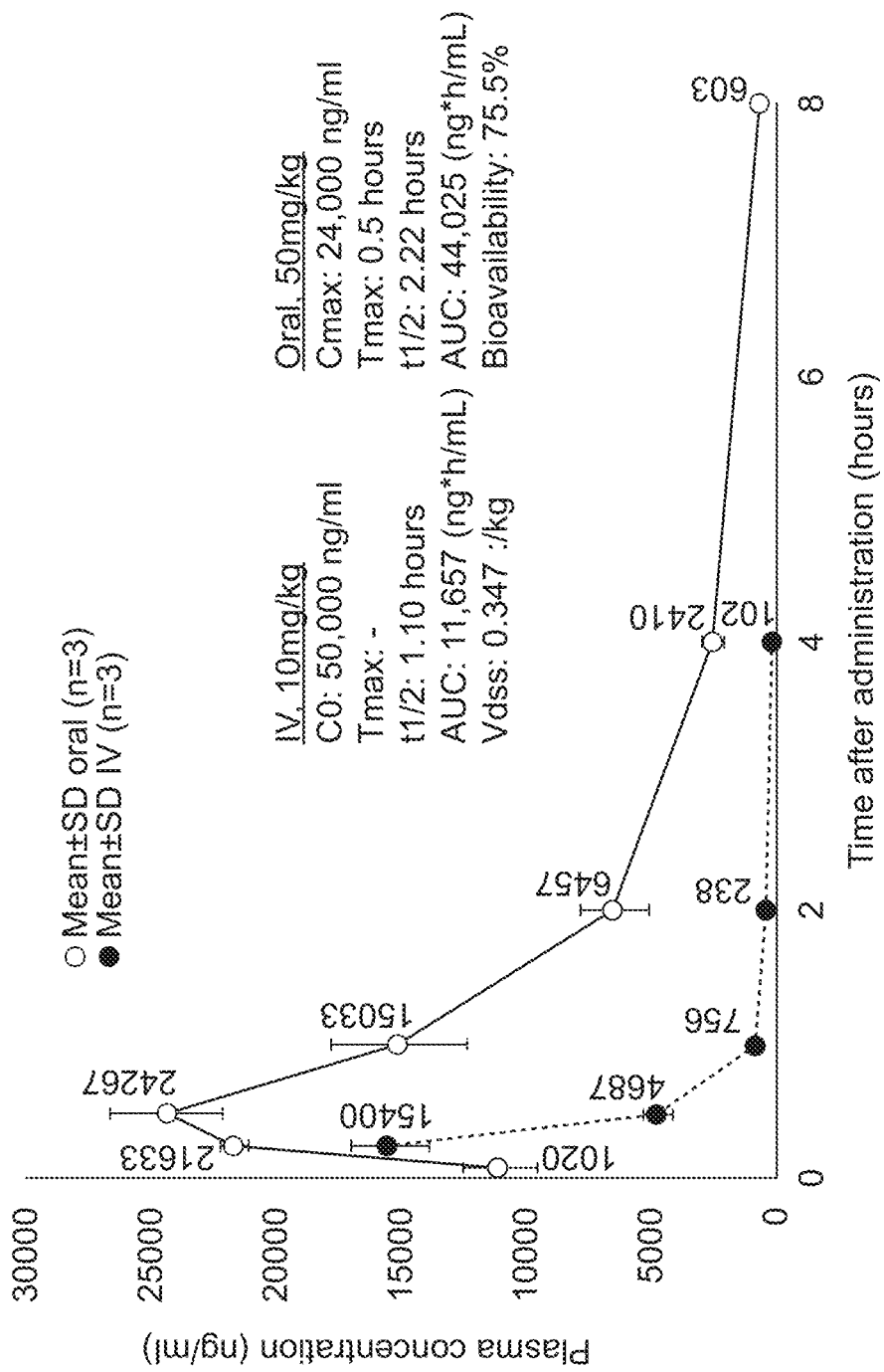
FIGS. 5A-5B shows the oral bioavailability and in vivo target engagement of trans-MiM 111 (Cpd 15B) (see e.g., Example 6).
Figure 5B:
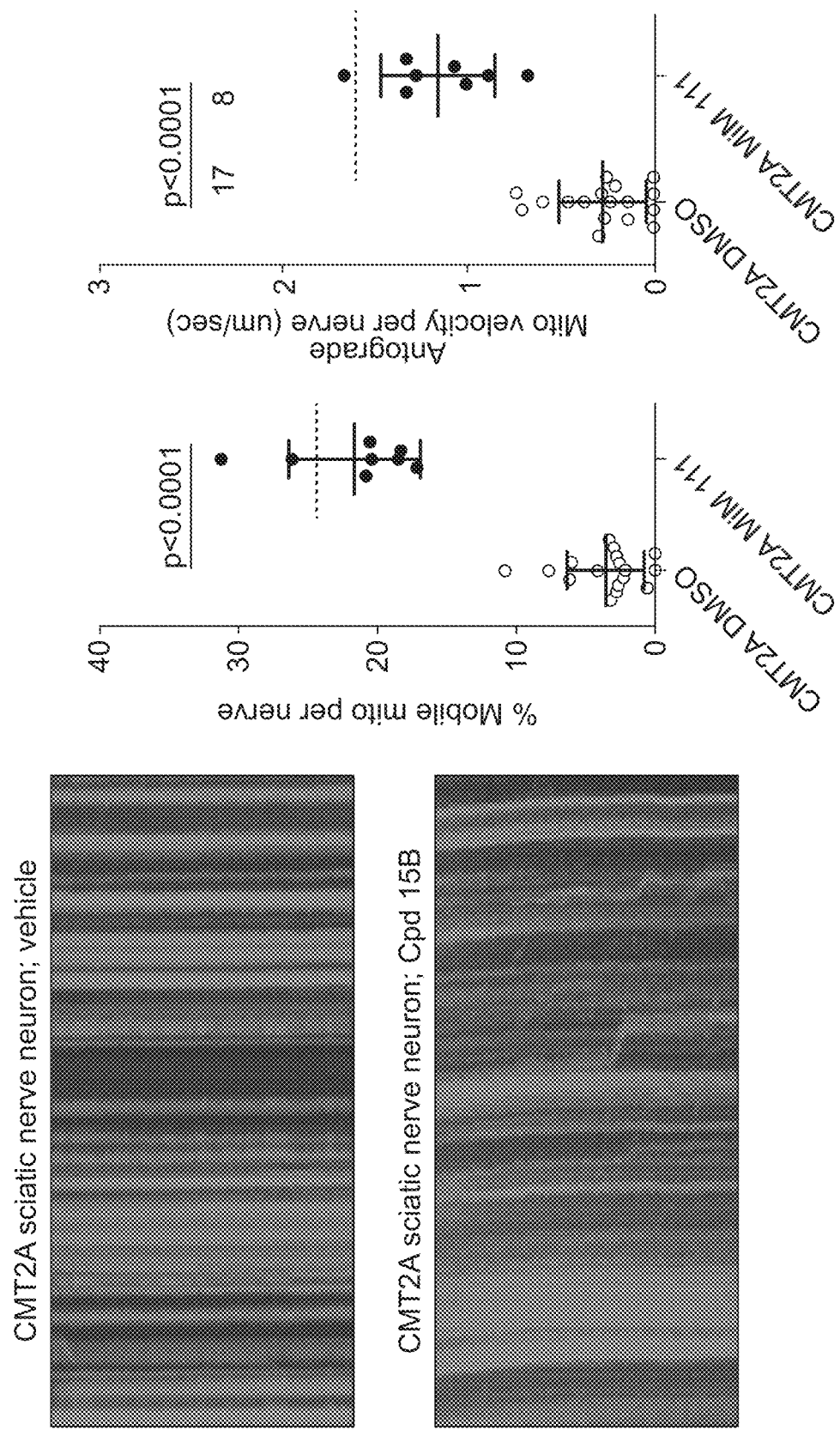

Example 6: In Vivo Trans-MiM 111 Engages its Mitochondrial Targets in a Pre-Clinical Mouse Model of CMT2A Taken together, the above results indicated that trans-MiM 111 has properties enabling it to activate mitofusins of neuronal mitochondria in CMT2A mice in vivo. In the only published study a prototype mitofusin activator, Chimera B-A/I, increased mitochondrial motility when topically applied to sciatic nerve neurons ex vivo (Rocha, A. G., et al.; Science 360:336-41, 2018). The in vivo effects of mitofusin activators on CMT2A neuronal mitochondria were never assessed because this chemical class of mitofusin agonists has a very short in vivo plasma half-life of ~0.2 hour. Because trans-MiM 111 is >75% orally bioavailable (FIG. 5A) its ability to engage peripheral nerve mitochondrial targets in vivo was assessed after a single oral dose. Transgenic mice expressing the human MFN2 T105M mutation in motor neurons (Rocha A. G., et al.; Science 360:336-41, 2018) received 50 mg/kg of trans-MiM 111 and mitochondrial motility in sciatic nerve neurons was assessed by a blinded investigator 6 hours thereafter. trans-MiM 111 markedly increased both the number and velocity of motile mitochondria in CMT2A mouse neurons (FIG. 5B).

Example 7: Off-Target, Specificity, and Safety Studies Show that Trans-MiM 111 has Properties of an Advanced Clinical Lead for CMT2A Off-target, specificity, and safety studies performed to determine the suitability of trans-MiM 111 for possible clinical translation (Table 4) demonstrated that it is a potent and selective mitofusin activator with a favorable drug profile. It exhibited sub-10 nM potency for both MFN1 and MFN2, with very low inhibitory activity for cytochrome P450 enzymes, indicating a small likelihood for drug-drug interactions. Activity screening against hERG, hNAV1.5, hKCNQ, and a panel of 42 receptors/kinases revealed only mild inhibition of dopamine amino transferase (DAT) and monoamine oxidase (MAO-A; ~30% inhibition at 10 µM), indicating a safety window of 1,000-fold compared to on-target efficacy, and a correspondingly limited potential for off-target side-effects.

TABLE 4

Summary of key properties of trans-MiM 111 (Compound 15B)

| On Target potency | |
|---|---|
| EC$_{50}$ Mfn1 KO cells (nM) | 7.7 |
| EC$_{50}$ Mfn2 KO cells (nM) | 9.5 |
| Physical properties | |
| MW/cLogP/TPSA | 289/3.22/49.33 Å |
| kinetic solubility (mM) | 175 |
| fsp3 (%) | 61 |

TABLE 4-continued

Summary of key properties of trans-MiM 111 (Compound 15B)

| Selectvity and safety profiles | |
|---|---|
| hNav1.5 (% inhib @ 10 mM) | 8.3 |
| nKCNQ (% inhib @ 10 mM) | 0 |
| hERG patch clamp IC$_{50}$ (mM) | >30 |
| 44 receptor/kinase panel (10 mM) | DAT and MAO-A >30% inhib |
| CYP1A2/2C9/2C19/2D6/3A4-M IC$_{50}$ (mM) | >50/>50/>50/>50/>50 |
| AMES test | negative |

Materials and Methods

Cell Lines

Wild-type MEFs were prepared from E10.5 c57/bl6 mouse embryos. SV-40 T antigen-immortalized MFN1 null (CRL-2992), MFN2 null (CRL-2993) and MFN1/MFN2 double null MEFs (CRL-2994) were purchased from ATCC. MEFs were subcultured in DMEM (4.5 g/L glucose) plus 10% fetal bovine serum, 1× nonessential amino acids, 2 mM L-glutamine, 100 units/mL penicillin and 100 µg/mL streptomycin.

Confocal Live Cell Studies of Mitochondria

Live cell imaging was performed on an Olympus Diaphot 200 fluorescence microscope equipped with a 60× water immersion objective. All live cells were grown on coated glass-bottom 12-well plates and studied in modified Krebs-Henseleit buffer (138 mM NaCl, 3.7 mM KCl, 1.2 mM KH$_2$PO$_4$, 15 mM, 20 mM HEPES and 1 mM CaCl$_2$)) at room temperature.

Cells were excited with 408 nm (Hoechst), 561 nm (MitoTracker Green and Calcein AM, GFP), or 637 nm (TMRE, MitoTracker Orange, Ethidium homodimer-1, and AF594-Dextran) laser diodes. For mitochondrial elongation studies, mitochondrial aspect ratio (long axis/short axis) was calculated using automated edge detection and Image J software. Mitochondrial depolarization was calculated as percent of green mitochondria visualized on MitoTracker Green and TMRE merged images, expressed as green/(green+yellow mitochondria)×100.

Preparative HPLC

Purification was performed using HPLC (H$_2$O-MeOH, Agilent 1260 Infinity systems equipped with DAD and mass-detectors. Waters SunFire C18 OBD Prep Column, 100 Å, 5 µm, 19 mm×100 mm with SunFire C18 Prep Guard Cartridge, 100 Å, 10 µm, 19 mm×10 mm) was used for separation. The material was dissolved in 0.7 mL DMSO. Flow rate: 30 mL/minute. Purity of the obtained fractions was checked via analytical LCMS. Spectra were recorded for each fraction as it was obtained straight after chromatography in the solution form. The solvent was evaporated in the flow of N$_2$ at 80° C. On the basis of post-chromatography LCMS analysis, fractions were combined united. Solid fractions were dissolved in 0.5 mL MeOH and transferred into pre-weighted marked vials. Obtained solutions were again evaporated in the flow of N$_2$ at 80° C. After drying, products were characterized by LCMS, $^1$H NMR, and $^{13}$C NMR.

HPLC/HRMS (ESI)

LC/MS analysis was carried out using Agilent 1100 Series LC/MSD system with DAD\ELSD and Agilent LC\MSD VL (G1956A), SL (G1956B) mass-spectrometer or Agilent 1200 Series LC/MSD system with DAD\ELSD and Agilent LC\MSD SL (G6130A), SL (G6140A) mass-spectrometer. All the LC/MS data were obtained using positive/negative mode switching. The compounds were separated using a Zorbax SB-C18 1.8 µm 4.6×15 mm Rapid Resolution cartridge (PN 821975-932) under a mobile phase (A—ACN, 0.1% formic acid; B—water (0.1% formic acid)). Flow rate: 3 mL/minute; Gradient 0 minutes—100% B; 0.01 minute—100% B; 1.5 minutes—0% B; 1.8 minutes—0% B; 1.81 minutes—100% B; Injection volume 1 µL; Ionization mode atmospheric pressure chemical ionization (APCI), Scan range m/z 80-1000.

Statistical Methods

Time-course and dose-response data are calculated for each study using GraphPad Prism. All data are reported as mean±SEM. Statistical comparisons (two-sided) used one-way ANOVA and Tukey's tests for multiple groups or Student's t-test for paired comparisons. $p<0.05$ was considered significant. In vitro pharmacokinetic analyses of mitofusin activators was performed at WuXi Apptec Co. Ltd.

Binding to human and CD-1 mouse plasma proteins was measured using equilibrium dialysis. Pooled individual frozen EDTA anticoagulated plasma mouse and human samples were used as test matrix. Warfarin was used as a positive control. The test compounds were spiked into blank matrix at the final concentration of 2 µM. A 150-µL aliquot of matrix sample was added to one side of the chamber in a 96-well equilibrium dialyzer plate (HTD dialysis) and an equal volume of dialysis buffer was added to the other side of the chamber. An aliquot of matrix sample was harvested before the incubation and used as $T_0$ samples for recovery calculation. The incubations were performed in triplicate. The dialyzer plate was placed in a humidified incubator and rotated slowly for four hours at 37° C. After incubation, the samples were taken from the matrix side as well as the buffer side. The plasma sample was matched with equal volume of blank buffer; and buffer samples were matched with equal volume of blank plasma. The matrix-matched samples were quenched with stop solution containing internal standard. All samples were analyzed by LC-MS/MS. All test compound concentrations in matrix and buffer samples are expressed as peak area ratios (PAR) of analyte/internal standard.

In vitro stability was measured in human and mouse liver microsomes. An intermediate solution (100 µM of small molecule) was initially prepared in methanol and subsequently used to prepare the working solution. This was achieved by a 10-fold dilution step of the intermediate solution in 100 mM potassium phosphate buffer. Ten microliters of a compound working solution or control working solution was added to all wells of a 96-well plate for the time points (minutes): $T_0$, $T_5$, $T_{10}$, $T_{20}$, $T_{30}$, $T_{60}$, NCF60, except the matrix blank. The microsome solution (680 µL/well) (#452117, Corning; Woburn, Mass., USA; #R1000, Xenotech; Kansas City, Kans., USA and #M1000, Xenotech; Kansas City, Kans., USA) was dispersed to 96-well plate as reservoir according to the plate map. Then, 80 µL/well was added to every plate by ADDA (Apricot Design Dual Arm, Apricot Designs, Inc., Covina, Calif., USA), and the mixture of microsome solution and compound were allowed to incubate at 37° C. for about 10 minutes. Next, 10 µL of 100 mM potassium phosphate buffer/well was added to NCF60 and incubated at 37° C. (timer 1H was started). After pre-warming, 90 µL/well of NADPH (#00616, Sigma, Aldrich, St. Louis, Mo., USA) regenerating system was dispensed to 96-well plate as reservoir according to the plate map. Then 10 µL/well was added to every plate by ADDA to start reaction. To terminate the reaction, 300 µL/well of stop solution (cold in 4° C., including 100 ng/mL tolbutamide and 100 ng/mL labetalol as internal standards) was used, and sampling plates were agitated for approximately 10 minutes. The samples were next centrifuged at 4000 rpm for 20 minutes at 4° C. Supernatants were analyzed by LC-MS/MS.

Parallel Artificial Membrane Permeability Assay (PAMPA)

A 10 µM solution of a small molecule in 5% DMSO (150 µL) was added to each well of the donor plate, whose PVDF membrane was pre-coated with 5 µL of 1% brain polar lipid extract (porcine)/dodecane mixture. Then, 300 µL of PBS was added to each well of the PTFE acceptor plate. The donor plate and acceptor plate were combined together and incubated for 4 hours at room temperature with shaking at 300 rpm. To prepare the $T_0$ sample, 20 µL of a donor solution was transferred to new well, followed by the addition of 250 µL PBS (DF: 13.5) and 130 µL of ACN (containing internal standard) as the $T_0$ sample. To prepare the acceptor sample, the plate was removed from incubator and 270 µL of the solution was transferred from each acceptor well and mixed with 130 µL ACN (containing internal standard) as an acceptor sample. To prepare the donor sample, 20 µL of the solution was transferred from each donor well and mixed with 250 µL PBS (DF: 13.5), 130 µL ACN (containing internal standard) as a donor sample. The acceptor samples and donor samples were analyzed by LC-MS/MS.

The present invention is also directed to the following clauses.

Clause 1:

A method of treating a peripheral nervous system (PNS) or central nervous system (CNS) genetic disorder, physical damage, and/or chemical injury, comprising: administering to a subject a therapeutically effective amount of a composition comprising one or more of a trans-stereoisomer 6-phenylhexanamide derivative mitofusin activator or a pharmaceutically acceptable salt thereof, wherein the trans-stereoisomer 6-phenylhexanamide derivative mitofusin activator stimulates mitochondrial fusion, increases mitochondrial fitness, and enhances mitochondrial subcellular transport.

Clause 2.

The method of clause 1, wherein the composition comprises one or more mitofusin activators, wherein the mitofusin activator comprises a structure of formula:

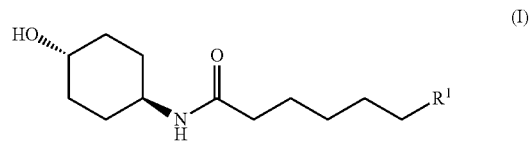

(I)

or a pharmaceutically acceptable salt, tautomer, or stereoisomer thereof, wherein $R^1$ is a non-, mono-, or poly-substituted $C_{3-8}$ cycloalkyl, $C_{3-8}$ heteroaryl, $C_{3-8}$ aryl, or $C_{3-8}$ heterocyclyl.

Clause 3:

The method of any of clauses 1 to 2, wherein the mitofusin activator comprises a structure of formula:

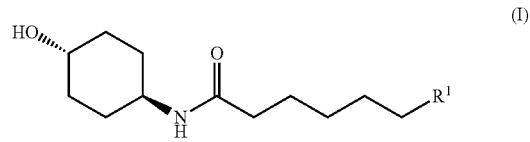

(I)

and wherein R¹ is

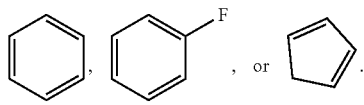

Clause 4.

The method of any of clauses 1 to 3, wherein R¹ is independently and optionally substituted by one or more of acetamide, $C_{1-8}$ alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene; wherein R¹ is optionally further substituted with one or more acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfone, sulfur dioxide, and/or thiophene; and wherein one or more of the alkyl, cycloalkyl, heteroaryl, heterocyclyl, indole, or phenyl substituent is optionally further substituted with one or more of the following substituents: acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and thiophene.

Clause 5.

The method of any of clauses 1 to 4, wherein the mitofusin activator is:

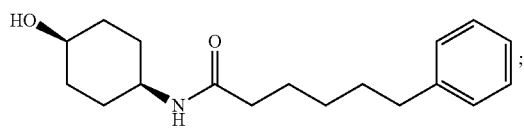

N-(trans-4-hydroxycyclohexyl)-6-phenylhexanamide

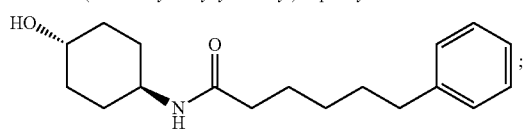

N-(trans-4-hydroxycyclohexyl)-6-phenylhexanamide

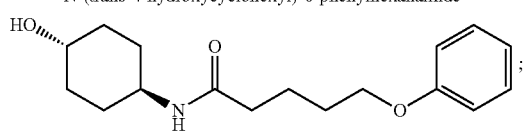

N-(trans-4-hydroxycyclohexyl)-5-phenoxypentanamide

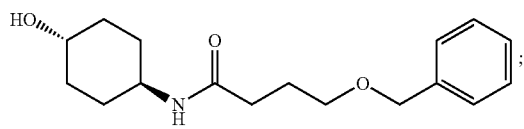

4-(benzyloxy)-N-(trans-4-hydroxycyclohexyl)-4-butanamide

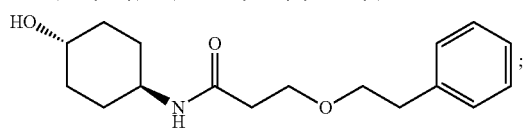

N-(trans-4-hydroxycyclohexyl)-3-phenethoxypropanamide

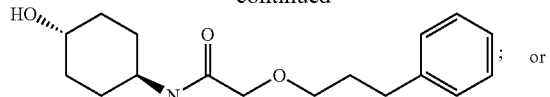

N-(trans-4-hydroxycyclohexyl)-2-(3-phenylpropoxy)acetamide

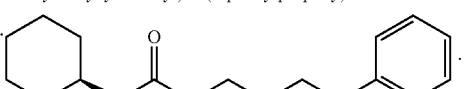

4-phenylbutyl (trans-4-hydroxycyclohexyl)carbamate

Clause 6.

A compound of Formula II

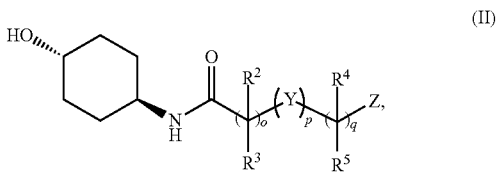

or a pharmaceutically acceptable salt thereof, wherein

Z is cycloalkyl, heterocycloalkyl, aryl, or heteroaryl;

$R^2$ and $R^3$ are independently selected from H, F, alkyl, and $C_{3-7}$ cycloalkyl, or $R^2$ and $R^3$ are taken together to form a $C_{3-7}$ cycloalkyl or heterocycloalkyl;

$R^4$ and $R^5$ are independently selected from H, F, alkyl, and $C_{3-7}$ cycloalkyl or $R^4$ and $R^5$ are taken together to form a $C_{3-7}$ cycloalkyl or heterocycloalkyl;

Y is O, $CR^6R^7$, $CR^8=CR^9$, a triple bond, cycloalkyl, heterocycloalkyl, aryl, heteroaryl, $NR^8$, S, $SO_2$, $SONR^9$, —$NR^9SO_2$—, —$NR^8CO$—, —$CONR^8$—, or —$NR^8CONR^9$—;

$R^6$ is H, F, alkyl, or cycloalkyl; and $R^7$ is H, F, alkyl, or cycloalkyl; or $R^6$ and $R^7$ are taken together to form $C_{3-7}$ cycloalkyl or heterocycloalkyl;

$R^8$ is H, alkyl, or $C_{3-7}$ cycloalkyl;

$R^9$ is H, alkyl, or $C_{3-7}$ cycloalkyl;

o is 0, 1, 2, 3, 4 or 5;

p is 0 or 1; and q is 0, 1, 2, 3, 4 or 5, wherein when o is equal to or greater than 1, then Y=$NR^8$, S, $SO_2$, $SONR^9$, —$NR^9SO_2$—, —$NR^8CO$—, —$CONR^8$—, —$NR^8CONR^9$—, and the sum of o+p+q is not less than 3 or greater than 7.

Clause 7.

The compound of clause 6, or a pharmaceutically acceptable salt thereof, wherein Z is cycloalkyl, heterocycloalkyl, aryl, or heteroaryl;

Y is O, $CR^6R^7$, cycloalkyl, or aryl;

$R^2$, $R^3$, $R^4$, $R^5$, $R^6$, $R^7$ and $R^8$ are independently selected from H and alkyl;

o is 0, 1, 2, 3, 4 or 5;

p is 0 or 1; and q is 0, 1, 2, 3, 4 or 5;

wherein when o is equal to or greater than 1, then X is S or $SO_2$; and wherein the sum of o+p+q is not less than 3 or greater than 7.

Clause 8.

The compound of any of clauses 6 to 7, or a pharmaceutically acceptable salt thereof, wherein Z is aryl or heteroaryl;
Y is O, $CH_2$, or cycloalkyl;
$R^2$, $R^3$, $R^4$, and $R^5$ are $CH_2$;
$R^8$ is H, alkyl, or $C_{3-7}$ cycloalkyl;
$R^9$ is or H, alkyl, and $C_{3-7}$ cycloalkyl;
o is 0, 1, 2, 3, 4 or 5;
p is 0 or 1; and
q is 0, 1, 2, 3, 4 or 5;
wherein when o is equal to or greater than 1, then X is S or $SO_2$, and
wherein the sum of o+p+q is not less than 3 or greater than 5.

Clause 9.

The compound of any of clauses 6 to 8, or a pharmaceutically acceptable salt thereof, wherein
Z is aryl or heteroaryl;
Y is cyclopropyl or cyclobutyl;
$R^2$, $R^3$, $R^4$, and $R^5$ are $CH_2$;
$R^8$ is H, alkyl, or $C_{3-7}$ cycloalkyl;
$R^9$ is H, alkyl, $COR^7$, or $C_{3-7}$ cycloalkyl;
or $R^8$ and $R^9$ are taken together to form $C_{3-7}$ cycloalkyl;
o is 0, 1, 2, or 3;
p is 1; and
q is 0, 1, 2, or 3;
wherein the sum of o+p+q is not less than 3 or greater than 5.

Clause 10.

The compound of any of clauses 6 to 9, or a pharmaceutically acceptable salt thereof, wherein
Z is aryl or heteroaryl;
Y is O or $CH_2$;
$R^2$, $R^3$, $R^4$, and $R^5$ are $CH_2$;
$R^8$ is H, alkyl, or $C_{3-7}$ cycloalkyl; $R^9$ is H, alkyl, $COR^7$ or $C_{3-7}$ cycloalkyl; or $R^8$ and $R^9$ are taken together to form $C_{3-7}$ cycloalkyl;
o is 0, 1, 2, 3 or 4;
p is 1; and
q is 0, 1, 2, 3 or 4;
wherein the sum of o+p+q is 5.

Clause 11.

The compound of any of clauses 6 to 10, or a pharmaceutically acceptable salt thereof, wherein
Z is aryl or heteroaryl;
Y is O or $CH_2$;
$R^2$, $R^3$, $R^4$, and $R^5$ are $CH_2$;
o is 0, 1, 2, 3 or 4;
p is 1; and
q is 0, 1, 2, 3 or 4;
wherein the sum of o+p+q is 5.

Clause 12.

The compound of any of clauses 6 to 11, or a pharmaceutically acceptable salt thereof, wherein
Z is phenyl or heteroaryl; wherein the heterocyclic moiety contains 1 to 4 atoms independently selected from nitrogen, oxygen and sulfur, and wherein the phenyl or heterocyclic moiety has 0 to 4 substituents independently selected from $R^8$, $OR^8$, Cl, F, —CN, $CF_3$, —$NR^8R^9$, —$SO_2NR^8R^9$, —$NR^8SO_2R^9$, —$SO_2R^9$, —$CONR^8R^{10}$, —$NR^8COR^{10}$, $C_{3-7}$ cycloalkyl, and heterocycloalkyl;
Y is O or $CH_2$;
$R^2$, $R^3$, $R^4$, and $R^5$ are $CH_2$;
$R^8$ is H, alkyl, or $C_{3-7}$ cycloalkyl; $R^9$ is H, alkyl, $COR^7$ or $C_{3-7}$ cycloalkyl; or $R^8$ and $R^9$ are taken together to form $C_{3-7}$ cycloalkyl;
$R^{10}$ is independently selected from alkyl or $C_{3-7}$ cycloalkyl;
o is 0, 1, 2, 3 or 4;
p is 1; and
q is 0, 1, 2, 3 or 4;
wherein the sum of o+p+q is 5.

Clause 13.

The compound of any of clauses 6 to 12, or a pharmaceutically acceptable salt thereof, wherein
Z is phenyl or heteroaryl; wherein the heterocyclic moiety contains 1 to 3 atoms independently selected from nitrogen, oxygen and sulfur, and wherein the phenyl or heterocyclic moiety has 0 to 3 substituents independently selected from $R^8$, $OR^8$, Cl, F, —CN, $CF_3$, —$NR^8R^9$, —$SO_2R^9$, —$CONR^8R^9$, —$NR^7COR^{10}$, $C_{3-7}$ cycloalkyl, and heterocycloalkyl;
Y is O or $CH_2$;
$R^2$, $R^3$, $R^4$, and $R^5$ are $CH_2$;
$R^8$ is H, alkyl, or $C_{3-7}$ cycloalkyl; $R^9$ is H, alkyl, $COR^7$ or $C_{3-7}$ cycloalkyl; or $R^8$ and $R^9$ are taken together to form $C_{3-7}$ cycloalkyl;
$R^{10}$ is alkyl or $C_{3-7}$ cycloalkyl;
o is 0, 1, 2, 3 or 4;
p is 1; and
q is 0, 1, 2, 3 or 4;
wherein the sum of o+p+q is 5.

Clause 14.

The compound of any of clauses 6 to 13, or a pharmaceutically acceptable salt thereof, wherein
Z is phenyl, 2-pyridinyl, 3-pyridinyl, 4-pyridinyl, 6-pyrimidinyl, 5-pyrimidinyl, 4-pyrimidinyl or 2-pyrimidinyl, wherein the phenyl, pyridinyl, and pyrimidinyl moiety has 0 to 2 substituents independently selected from $R^8$, $OR^8$, Cl, F, —CN, $CF_3$, —$NR^8R^9$, —$SO_2R^{10}$, —$CONR^8R^9$, and —$NR^8COR^{10}$
Y is O or $CH_2$;
$R^2$, $R^3$, $R^4$, and $R^5$ are $CH_2$;
$R^8$ is H, alkyl, or $C_{3-7}$ cycloalkyl;
$R^9$ is H, alkyl, $COR^7$ or $C_{3-7}$ cycloalkyl; or
$R^8$ and $R^9$ are taken together to form $C_{3-7}$ cycloalkyl;
$R^{10}$ is alkyl or $C_{3-7}$ cycloalkyl;
o is 0, 1, 2, 3 or 4;
p is 1; and
q is 0, 1, 2, 3 or 4;
wherein the sum of o+p+q is 5.

Clause 15.

The compound of any of clauses 6 to 14, or a pharmaceutically acceptable salt thereof, wherein
Z is phenyl, 2-pyridinyl, 3-pyridinyl, 4-pyridinyl, 6-pyrimidinyl, 5-pyrimidinyl, 4-pyrimidinyl or 2-pyrimidinyl, wherein the phenyl, pyridinyl, and pyrimidinyl moiety has 0 to 2 substituents independently selected from $R^8$, $OR^8$, Cl, F, —CN, $CF_3$, —$NR^8R^9$, —$SO_2R^{10}$, —$CONR^8R^9$, and —$NR^8COR^{10}$
Y is O or $CH_2$;
$R^2$, $R^3$, $R^4$, and $R^5$ are $CH_2$;
$R^8$ is H, alkyl, or $C_{3-7}$ cycloalkyl; $R^9$ is H, alkyl, $COR^7$ or $C_{3-7}$ cycloalkyl; or
$R^8$ and $R^9$ are taken together to form $C_{3-7}$ cycloalkyl;
$R^{10}$ is alkyl or $C_{3-7}$ cycloalkyl;
o is 0, 1, 2, 3 or 4;
p is 1; and
q is 0, 1, 2, 3 or 4;
wherein the sum of o+p+q is 5.

Clause 16.

The compound of any of clauses 6 to 15, or pharmaceutically acceptable salt thereof, wherein the compound is

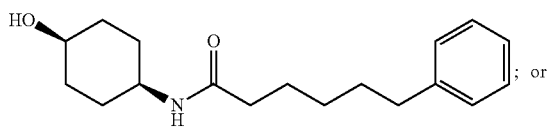

N-(cis-4-hydroxycyclohexyl)-6-phenylhexanamide

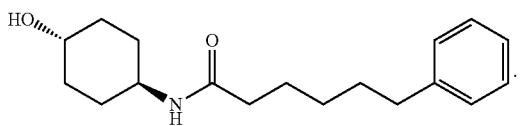

N-(trans-4-hydroxycyclohexyl)-6-phenylhexanamide

Clause 17.

The compound of any of clauses 6 to 15, or pharmaceutically acceptable salt thereof, wherein the compound is:

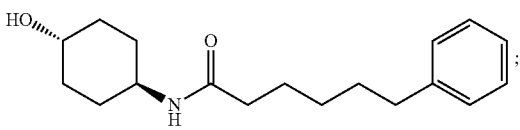

N-(trans-4-hydroxycyclohexyl)-6-phenylhexanamide

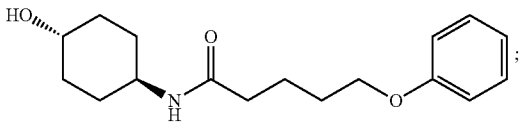

N-(trans-4-hydroxycyclohexyl)-5-phenoxypentanamide

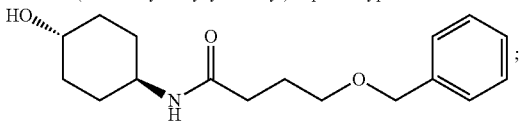

4-(benzyloxy)-N-(trans-4-hydroxycyclohexyl)-4-butanamide

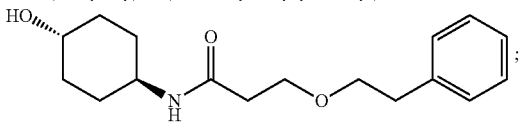

N-(trans-4-hydroxycyclohexyl)-3-phenethoxypropanamide

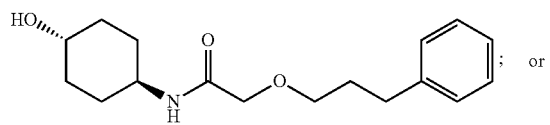

N-(trans-4-hydroxycyclohexyl)-2-(3-phenylpropoxy)acetamide

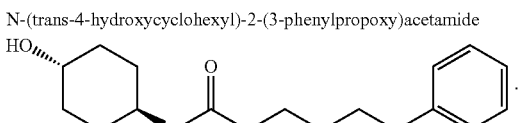

4-phenylbutyl (trans-4-hydroxycyclohexyl)carbamate

Clause 18.

A method of treating a disease for which a mitofusin activator is indicated, the method comprising administering to a mammal in need thereof a therapeutically effective amount of a compound of Formula II

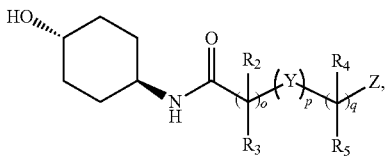

(II)

or a pharmaceutically acceptable salt thereof, wherein

Z is cycloalkyl, heterocycloalkyl, aryl, or heteroaryl;

$R^2$ and $R^3$ are independently selected from H, F, alkyl, and $C_{3-7}$ cycloalkyl, or $R^2$ and $R^3$ are taken together to form a $C_{3-7}$ cycloalkyl or heterocycloalkyl;

$R^4$ and $R^5$ are independently selected from H, F, alkyl, and $C_{3-7}$ cycloalkyl or $R^4$ and $R^5$ are taken together to form a $C_{3-7}$ cycloalkyl or heterocycloalkyl;

Y is O, $CR^6R^7$, $CR^8$=$CR^9$, a triple bond, cycloalkyl, heterocycloalkyl, aryl, heteroaryl, $NR^8$, S, $SO_2$, $SONR^9$, —$NR^9SO_2$—, —$NR^8CO$—, —$CONR^8$—, or —$NR^8CONR^9$—;

$R^6$ is H, F, alkyl, or cycloalkyl; and $R^7$ is H, F, alkyl, or cycloalkyl; or $R^6$ and $R^7$ are taken together to form $C_{3-7}$ cycloalkyl or heterocycloalkyl;

$R^8$ is H, alkyl, or $C_{3-7}$ cycloalkyl;

$R^9$ is H, alkyl, or $C_{3-7}$ cycloalkyl;

o is 0, 1, 2, 3, 4 or 5;

p is 0 or 1; and q is 0, 1, 2, 3, 4 or 5, wherein when o is equal to or greater than 1, then Y=$NR^8$, S, $SO_2$, $SONR^9$, —$NR^9SO_2$—, —$NR^8CO$—, —$CONR^8$—, —$NR^8CONR^9$—, and the sum of o+p+q is not less than 3 or greater than 7.

Clause 19.

The method of any of clauses 1-5 or 18, wherein the PNS or CNS disorder is selected from any one or a combination of:

a chronic neurodegenerative condition wherein mitochondrial fusion, fitness, or trafficking are impaired;

a disease or disorder associated with mitofusin 1 (MFN1) or mitofusin 2 (MFN2) dysfunction;

a disease associated with mitochondrial fragmentation, dysfunction, or dysmotility;

a degenerative neuromuscular condition such as Charcot-Marie-Tooth disease, Amyotrophic Lateral Sclerosis, Huntington's disease, Alzheimer's disease, Parkinson's disease;

hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, or pyruvate dehydrogenase complex deficiency (PDCD/PDH);

diabetic neuropathy;

chemotherapy-induced peripheral neuropathy; and/or crush injury, spinal cord injury (SCI), traumatic brain injury, stroke, optic nerve injury, and related conditions that involve axonal disconnection.

Clause 20.

The method of any of clauses 1-5, 18 or 19, with the proviso that the mitofusin activator is not selected from the following compounds:

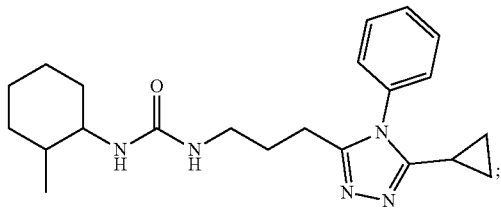

1-(3-(5-cyclopropyl-4-phenyl-4H-1,2,4-triazol-3-yl)propyl)-3-(2-methylcyclohexyl)urea (Chimera C)

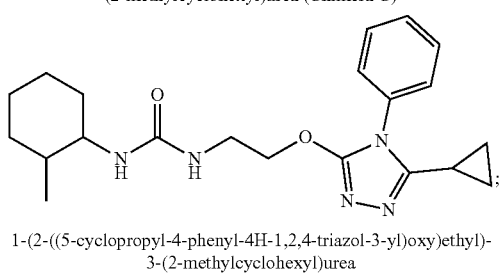

1-(2-((5-cyclopropyl-4-phenyl-4H-1,2,4-triazol-3-yl)oxy)ethyl)-3-(2-methylcyclohexyl)urea Clause 21.

The method of any of clauses 1-5 or 18-20, wherein the composition further comprises a pharmaceutically acceptable excipient.

Clause 22.

A method of treating a CNS or PNS genetic or non-genetic neurodegenerative condition, injury, damage, or trauma comprising administering to the subject a therapeutically effective amount of the compound of any one of clauses 6 to 17.

Clause 23.

The method of clause 22, wherein the subject is diagnosed with or is suspected of having:

a chronic neurodegenerative condition wherein mitochondrial fusion, fitness, or trafficking are impaired;

a disease or disorder associated with mitofusin 1 (MFN1) or mitofusin 2 (MFN2) dysfunction;

a disease associated with mitochondrial fragmentation, dysfunction, or dysmotility;

a degenerative neuromuscular condition such as Charcot-Marie-Tooth disease, Amyotrophic Lateral Sclerosis, Huntington's disease, Alzheimer's disease, Parkinson's disease;

hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), Mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial mhannelopathy, or pyruvate dehydrogenase complex deficiency (PDCD/PDH);

diabetic neuropathy;

chemotherapy-induced peripheral neuropathy; and/or crush injury, spinal cord injury, traumatic brain injury, stroke, optic nerve injury, and related conditions that involve axonal disconnection.

Clause 24.

A composition comprising the compound of any one of clauses 6 to 17 and a pharmaceutically acceptable excipient.

The present disclosure is also directed to the following embodiments:

A. Methods for treating a mitochondria-associated disease, disorder, or condition. The methods comprise: administering a therapeutically effective amount of a composition comprising one or more of mitofusin activator or a pharmaceutically acceptable salt thereof to a subject having or suspected of having a mitochondria-associated disease, disorder or condition, the mitofusin activator having a structure represented by the following formula:

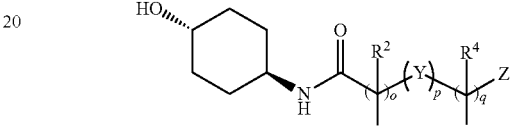

wherein:

Z is cycloalkyl, heterocycloalkyl, aryl, or heteroaryl;

$R^2$ and $R^3$ are independently selected from H, F, alkyl, and $C_{3-7}$ cycloalkyl, or $R^2$ and $R^3$ taken together form a $C_{3-7}$ cycloalkyl or heterocycloalkyl;

$R^4$ and $R^5$ are independently selected from H, F, alkyl, and $C_{3-7}$ cycloalkyl, or $R^4$ and $R^5$ taken together form a $C_{3-7}$ cycloalkyl or heterocycloalkyl;

Y is O, $CR^6R^7$, $CR^8$=$CR^9$, C≡C, cycloalkyl, heterocycloalkyl, aryl, heteroaryl, $NR^8$, S, $SO_2$, $SONR^9$, $NR^9SO_2$, $NR^8CO$, $CONR^8$, or $NR^8CONR^9$;

$R^6$ is H, F, alkyl, or cycloalkyl, $R^7$ is H, F, alkyl, or cycloalkyl, or $R^6$ and $R^7$ taken together form a $C_{3-7}$ cycloalkyl or heterocycloalkyl;

$R^8$ is H, alkyl, or $C_{3-7}$ cycloalkyl, $R^9$ is H, alkyl, or $C_{3-7}$ cycloalkyl, or $R^8$ and $R^9$ taken together form a $C_{3-7}$ cycloalkyl;

o is 0, 1, 2, 3, 4 or 5;

p is 0 or 1; and q is 0, 1, 2, 3, 4 or 5, provided that if Y is cycloalkyl and p is 1 the sum of o+p+q is not less than 3 or greater than 5, and otherwise the sum of o+p+q is 5.

B. Compositions comprising a mitofusin activator or a pharmaceutically acceptable salt thereof. The compositions comprise: a mitofusin activator or a pharmaceutically acceptable salt thereof, the mitofusin activator having a structure represented by the following formula:

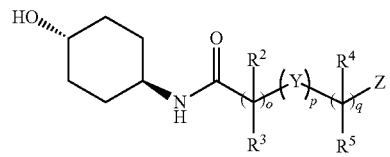

wherein:

Z is cycloalkyl, heterocycloalkyl, aryl, or heteroaryl;

$R^2$ and $R^3$ are independently selected from H, F, alkyl, and $C_{3-7}$ cycloalkyl, or $R^2$ and $R^3$ taken together form a $C_{3-7}$ cycloalkyl or heterocycloalkyl;

R⁴ and R⁵ are independently selected from H, F, alkyl, and C₃₋₇ cycloalkyl, or R⁴ and R⁵ taken together form a C₃₋₇ cycloalkyl or heterocycloalkyl;

Y is O, CR⁶R⁷, CR⁸=CR⁹, C≡C, cycloalkyl, heterocycloalkyl, aryl, heteroaryl, NR⁸, S, SO₂, SONR⁹, NR⁹SO₂, NR⁸CO, CONR⁸, or NR⁸CONR⁹;

R⁶ is H, F, alkyl, or cycloalkyl, R⁷ is H, F, alkyl, or cycloalkyl, or R⁶ and R⁷ taken together form a C₃₋₇ cycloalkyl or heterocycloalkyl;

R⁸ is H, alkyl, or C₃₋₇ cycloalkyl, R⁹ is H, alkyl, or C₃₋₇ cycloalkyl, or R⁸ and R⁹ taken together form a C₃₋₇ cycloalkyl;

o is 0, 1, 2, 3, 4 or 5;

p is 0 or 1; and q is 0, 1, 2, 3, 4 or 5, provided that if Y is cycloalkyl and p is 1 the sum of o+p+q is not less than 3 or greater than 5, and otherwise the sum of o+p+q is 5.

Embodiments A and B may include one or more of the following elements:

Element 1: wherein:
Z is aryl or heteroaryl;
Y is O, CR⁶R⁷, or cycloalkyl;
R², R³, R⁴, R⁵, R⁶, and R⁷ are independently selected from H and alkyl; and
p is 1.

Element 2: wherein:
Y is cyclopropyl or cyclobutyl;
R², R³, R⁴ and R⁵ are H;
o is 0, 1, 2, or 3;
p is 1; and
q is 0, 1, 2 or 3.

Element 3: wherein:
Y is O or CH₂;
R², R³, R⁴ and R⁵ are H; and
p is 1.

Element 4: wherein Z is phenyl or heteroaryl, the heteroaryl containing 1 to 4 atoms independently selected from nitrogen, oxygen and sulfur, and the phenyl or the heteroaryl having 0 to 4 substituents independently selected from R⁸, OR⁸, Cl, F, CN, CF₃, NR⁸R⁹, SO₂NR⁸R⁹, NR⁸SO₂R⁹, SO₂R⁹, CONR⁸R¹⁰, NR⁸COR¹⁰, C₃₋₇ cycloalkyl, and heterocycloalkyl; wherein R¹⁰ is alkyl or C₃₋₇ cycloalkyl.

Element 5: Z is phenyl, 2-pyridinyl, 3-pyridinyl, 4-pyridinyl, 6-pyrimidinyl, 5-pyrimidinyl, 4-pyrimidinyl or 2-pyrimidinyl, Z having 0 to 2 substituents independently selected from R⁸, OR⁸, Cl, F, CN, CF₃, NR⁸R⁹, SO₂R¹⁰, CONR⁸R⁹, and NR⁸COR¹⁰; wherein R¹⁰ is alkyl or C₃₋₇ cycloalkyl.

Element 6: wherein the mitofusin activator comprises a trans-stereoisomer 6-phenylhexanamide derivative or a pharmaceutically acceptable salt thereof; wherein the mitofusin activator stimulates mitochondrial fusion, increases mitochondrial fitness, and enhances mitochondrial subcellular transport.

Element 7: wherein the mitofusin activator has a structure represented by the following formula:

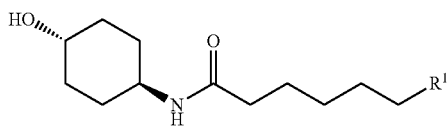

or a pharmaceutically acceptable salt, tautomer, or stereoisomer thereof; wherein R¹ is a non-, mono-, or poly-substituted C₃₋₈ cycloalkyl, C₃₋₈ heteroaryl, C₃₋₈ aryl, or C₃₋₈ heterocyclyl.

Element 8: wherein R¹ is

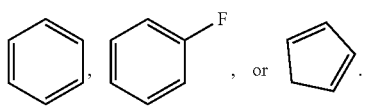

Element 9: wherein the mitofusin activator has a structure represented by one or more of the following formulas:

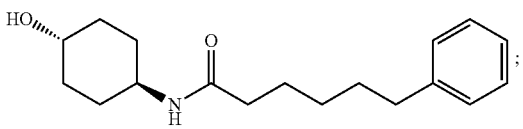

N-(trans-4-hydroxycyclohexyl)-6-phenylhexanamide

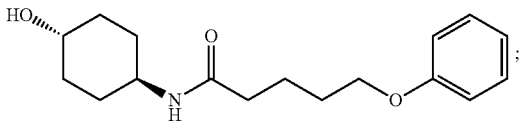

N-(trans-4-hydroxycyclohexyl)-5-phenoxypentanamide

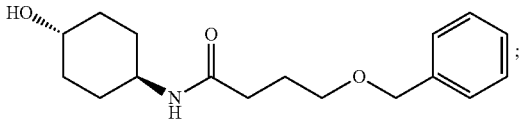

4-(benzyloxy)-N-(trans-4-hydroxycyclohexyl)-4-butanamide

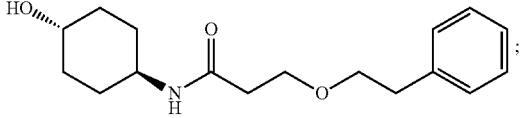

N-(trans-4-hydroxycyclohexyl)-3-phenethoxypropanamide

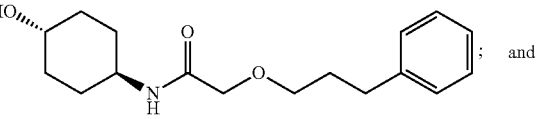

N-(trans-4-hydroxycyclohexyl)-2-(3-phenylpropoxy)acetamide

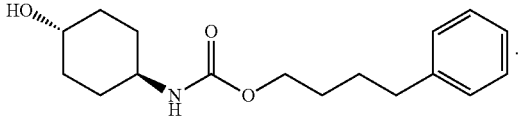

4-phenylbutyl (trans-4-hydroxycyclohexyl)carbamate

Element 10: wherein the mitochondria-associated disease, disorder or condition is a peripheral nervous system (PNS) or central nervous system (CNS) genetic or non-genetic disorder, physical damage, and/or chemical injury.

Element 11: wherein the PNS or CNS disorder is selected from any one or a combination of a chronic neurodegenerative condition wherein mitochondrial fusion, fitness, or trafficking are impaired; a disease or disorder associated with mitofusin 1 (MFN1) or mitofusin 2 (MFN2) dysfunction; a disease associated with mitochondrial fragmentation, dysfunction, or dysmotility; a degenerative neuromuscular condition such as Charcot-Marie-Tooth disease, Amyotrophic Lateral Sclerosis, Huntington's disease, Alzheimer's disease, Parkinson's disease; hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, or pyruvate dehydrogenase complex deficiency (PDCD/PDH); diabetic neuropathy; chemotherapy-induced peripheral neuropathy; crush injury, spinal cord injury (SCI), traumatic brain injury, stroke, optic nerve injury, and related conditions that involve axonal disconnection; and any combination thereof.

Element 12: wherein the composition further comprises a pharmaceutically acceptable excipient.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa. The term "and/or" as used in a phrase such as "A and/or B" herein is intended to include "A and B," "A or B," "A," and "B." Numerical ranges used herein include the numbers recited in the range. For example, the numerical range "from 1 wt % to 10 wt %" includes 1 wt % and 10 wt % within the recited range.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developers efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is:

1. A method comprising:
   administering a therapeutically effective amount of a composition comprising one or more of a mitofusin activator or a pharmaceutically acceptable salt thereof to a subject having or suspected of having a mitochondria-associated disease, disorder or condition, the mitofusin activator having a structure represented by the following formula:

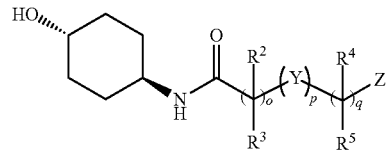

wherein:
Z is phenyl or substituted phenyl;
$R^2$ and $R^3$ are H;
$R^4$ and $R^5$ are H;
Y is O, $CH_2$ or cycloalkyl;
   wherein the cycloalkyl is cyclopropyl or cyclobutyl;
o is 0, 1, 2, 3, 4 or 5;
p is 0 or 1; and
q is 0, 1, 2, 3, 4 or 5, provided that if Y is cycloalkyl and p is 1 the sum of o+p+q is not less than 3 or greater than 5, and otherwise the sum of o+p+q is 5;

wherein the mitofusin activator comprises about 60% trans-stereoisomer or greater on a molar basis relative to cis-stereoisomer.

2. The method of claim 1, wherein:
Y is cyclopropyl or cyclobutyl;
o is 0, 1, 2, or 3;
p is 1; and
q is 0, 1, 2 or 3.

3. The method of claim 1, wherein the phenyl or substituted phenyl has 0 to 4 substituents independently selected from the group consisting of $R^8$, $OR^8$, Cl, F, CN, $CF_3$, $NR^8R^9$, $SO_2NR^8R^9$, $NR^8SO_2R^9$, $SO_2R^{10}$, $CONR^8R^9$, $NR^8COR^{10}$, $C_{3-7}$ cycloalkyl, and heterocycloalkyl;
wherein $R^8$ is H, alkyl, or $C_{3-7}$ cycloalkyl; $R^9$ is H, alkyl, or $C_{3-7}$ cycloalkyl; and $R^{10}$ is alkyl or $C_{3-7}$ cycloalkyl.

4. The method of claim 1, wherein the mitofusin activator comprises a trans-stereoisomer 6-phenylhexanamide derivative or a pharmaceutically acceptable salt thereof;
wherein the mitofusin activator stimulates mitochondrial fusion, increases mitochondrial fitness, and enhances mitochondrial subcellular transport.

5. The method of claim 1, wherein the mitofusin activator has a structure represented by the following formula:

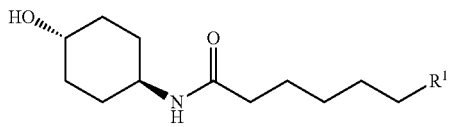

or a pharmaceutically acceptable salt, tautomer, or stereoisomer thereof;
wherein $R^1$ is phenyl or substituted phenyl.

6. The method of claim 5, wherein $R^1$ is

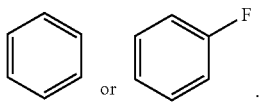.

7. The method of claim 1, wherein the mitofusin activator has a structure represented by one or more of the following formulas:

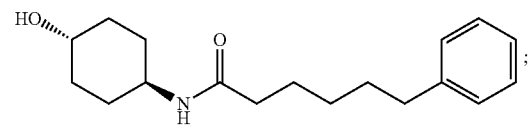

N-(trans-4-hydroxycyclohexyl)-6-phenylhexanamide

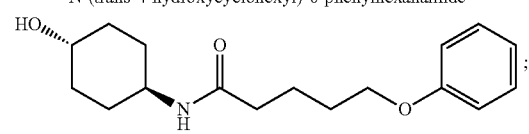

N-(trans-4-hydroxycyclohexyl)-5-phenoxypentanamide

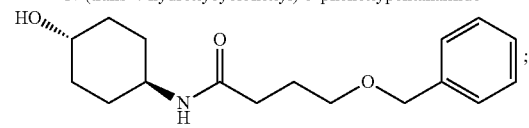

4-(benzyloxy)-N-(trans-4-hydroxycyclohexyl)-4-butanamide

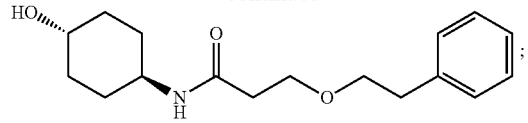

N-(trans-4-hydroxycyclohexyl)-3-phenethoxypropanamide

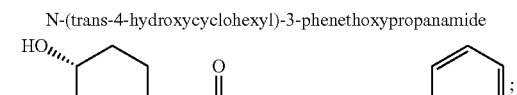

N-(trans-4-hydroxycyclohexyl)-2-(3-phenylpropoxy)acetamide

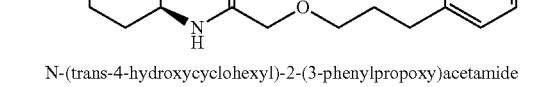

4-phenylbutyl (trans-4-hydroxycyclohexyl)carbamate

N-(trans-4-hydroxycyclohexyl)-2-(3-phenylpropyl)cyclopropane-1-carboxamide

8. The method of claim 1, wherein the mitochondria-associated disease, disorder or condition is a peripheral nervous system (PNS) or central nervous system (CNS) genetic or non-genetic disorder, physical damage, and/or chemical injury.

9. The method of claim 8, wherein the PNS or CNS disorder is selected from any one or a combination of a chronic neurodegenerative condition wherein mitochondrial fusion, fitness, or trafficking are impaired; a disease or disorder associated with mitofusin 1 (MFN1) or mitofusin 2 (MFN2) dysfunction; a disease associated with mitochondrial fragmentation, dysfunction, or dysmotility; a degenerative neuromuscular condition selected from Charcot-Marie-Tooth disease, Amyotrophic Lateral Sclerosis, Huntington's disease, Alzheimer's disease, and Parkinson's disease; hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, or pyruvate dehydrogenase complex deficiency (PDCD/PDH); diabetic neuropathy; chemotherapy-induced peripheral neuropathy; crush injury, spinal cord injury (SCI), traumatic brain injury, stroke, optic nerve injury, and related conditions that involve axonal disconnection; and any combination thereof.

10. A composition comprising:
a mitofusin activator or a pharmaceutically acceptable salt thereof, the mitofusin activator having a structure represented by the following formula:

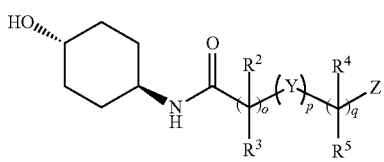

wherein:
Z is phenyl or substituted phenyl;
R² and R³ are H;
R⁴ and R⁵ are H;
Y is O, CH₂ or cycloalkyl;
  wherein the cycloalkyl is cyclopropyl or cyclobutyl;
o is 0, 1, 2, 3, 4 or 5;
p is 0 or 1; and
q is 0, 1, 2, 3, 4 or 5, provided that if Y is cycloalkyl and p is 1 the sum of o+p+q is not less than 3 or greater than 5, and otherwise the sum of o+p+q is 5;
  wherein the mitofusin activator comprises about 60% trans-stereoisomer or greater on a molar basis relative to cis-stereoisomer.

11. The composition of claim 10, wherein:
Y is cyclopropyl or cyclobutyl;
o is 0, 1, 2, or 3;
p is 1; and
q is 0, 1, 2 or 3.

12. The composition of claim 10, wherein the phenyl or substituted phenyl has 0 to 4 substituents independently selected from the group consisting of R⁸, OR⁸, Cl, F, CN, CF₃, NR⁸R⁹, SO₂NR⁸R⁹, NR⁸SO₂R⁹, SO₂R¹⁰, CONR⁸R⁹, NR⁸COR¹⁰, C₃₋₇ cycloalkyl, and heterocycloalkyl;
  wherein R⁸ is H, alkyl, or C₃₋₇ cycloalkyl; R⁹ is H, alkyl, or C₃₋₇ cycloalkyl; and R¹⁰ is alkyl or C₃₋₇ cycloalkyl.

13. The composition of claim 10, wherein the mitofusin activator has a structure represented by the following formula:

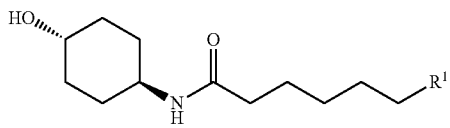

or a pharmaceutically acceptable salt, tautomer, or stereoisomer thereof;
wherein R¹ is phenyl or substituted phenyl.

14. The composition of claim 13, wherein R¹ is

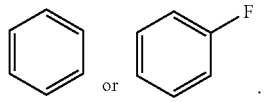

15. The composition of claim 10, wherein the mitofusin activator has a structure represented by one or more of the following formulas:

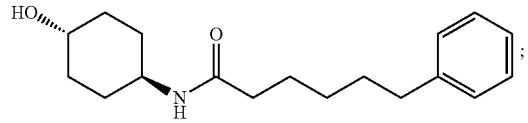

N-(trans-4-hydroxycyclohexyl)-6-phenylhexanamide

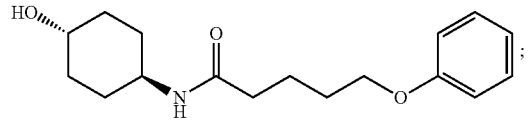

N-(trans-4-hydroxycyclohexyl)-5-phenoxypentanamide

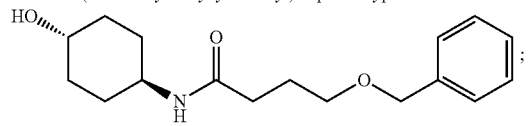

4-(benzyloxy)-N-(trans-4-hydroxycyclohexyl)-4-butanamide

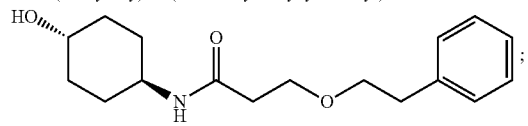

N-(trans-4-hydroxycyclohexyl)-3-phenethoxypropanamide

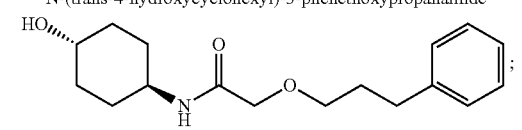

N-(trans-4-hydroxycyclohexyl)-2-(3-phenylpropoxy)acetamide

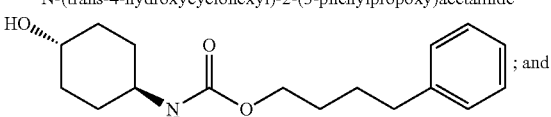

4-phenylbutyl (trans-4-hydroxycyclohexyl)carbamate

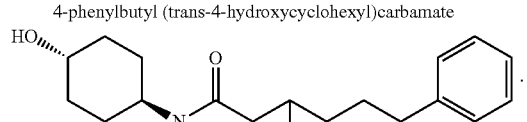

N-(trans-4-hydroxycyclohexyl)-2-(3-phenylpropyl)cyclopropane-1-carboxamide

16. The composition of claim 10, further comprising:
a pharmaceutically acceptable excipient.

17. The method of claim 1, wherein the mitofusin activator comprises about 95% trans-stereoisomer or greater on a molar basis relative to cis-stereoisomer.

18. The composition of claim 10, wherein the mitofusin activator comprises about 95% trans-stereoisomer or greater on a molar basis relative to cis-stereoisomer.

* * * * *